US 6,602,070 B2

(12) United States Patent
Miller et al.

(10) Patent No.: US 6,602,070 B2
(45) Date of Patent: *Aug. 5, 2003

(54) SYSTEMS AND METHODS FOR DENTAL TREATMENT PLANNING

(75) Inventors: Ross J. Miller, Sunnyvale, CA (US); Muhammad Chishti, Sunnyvale, CA (US); Huafeng Wen, Redwood Shores, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/843,246

(22) Filed: Apr. 25, 2001

(65) Prior Publication Data

US 2002/0042038 A1 Apr. 11, 2002

Related U.S. Application Data

(63) Continuation-in-part of application No. 09/313,289, filed on May 13, 1999, now Pat. No. 6,318,994.
(60) Provisional application No. 60/199,610, filed on Apr. 25, 2000.

(51) Int. Cl.[7] ................................................ A61C 3/00
(52) U.S. Cl. ........................................ 433/24; 433/213
(58) Field of Search .......................... 433/24, 213, 214

(56) References Cited

U.S. PATENT DOCUMENTS

| 4,037,324 A | * | 7/1977 | Andreasen ................... 433/24 |
| 5,340,309 A | * | 8/1994 | Robertson .................... 433/69 |
| 5,454,717 A | * | 10/1995 | Andreiko et al. ............. 433/24 |
| 5,542,842 A | | 8/1996 | Andreiko et al. |
| 5,549,476 A | | 8/1996 | Stern |
| 5,587,912 A | | 12/1996 | Andersson et al. |
| 5,605,459 A | | 2/1997 | Kuroda et al. |
| 5,607,305 A | | 3/1997 | Andersson et al. |
| 5,645,421 A | | 7/1997 | Slootsky |
| 6,217,334 B1 | | 4/2001 | Hultgren |

FOREIGN PATENT DOCUMENTS

| FR | 2 369828 | 6/1978 |
| WO | WO94/10935 | 5/1994 |
| WO | WO98/32394 | 7/1998 |

OTHER PUBLICATIONS

Biostar Operation & Training Manual, Great Lakes Orthodontics, Ltd. 199 Fire Tower Drive, Tonawanda, New York, 14150–5890.
Chiappone, "Constructing the gnathologic setup and positioner," *J.Clin. Orthod.*, 1980, 14:121–133.
Cottingham, "Gnathologic clear plastic positioner," *Am. J. Orthod.*, 1969, 55:23–31.
Cureton, "Correcting malaligned mandibular incisors with removable retainers," *J.Clin. Orthod.* 1996, 30:390–395.
Doyle, "Digital Dentistry" *Computer Graphics World* (Oct. 2000) pp. 50–52, 54.
Elsasser, "Some observations on the history and uses of the Kesling positioner," *Am. J. Orthod.* 1950, 36:368–374.
Kamada et al., "Case reports on tooth positioners with LTV vinyl silicone rubber and some case reports," *J. Nihon University School of Dentistry* 1982, 24(1): 1–27.
Kesling, "The philosophy of the tooth positioning appliance," *Am. J. Orthod. Oral. Surg.* 1945, 31(6):297–304.

(List continued on next page.)

*Primary Examiner*—John J. Wilson
(74) *Attorney, Agent, or Firm*—Townsend and Townsend and Crew LLP; Bao Tran, Esq.

(57) ABSTRACT

Computer-implemented systems and methods implement a dental treatment plan by specifying tooth movement patterns using a two-dimensional array; and generating treatment paths to move the teeth in accordance with the specified pattern.

65 Claims, 17 Drawing Sheets

OTHER PUBLICATIONS

Kesling, "Coordinating the predetermined pattern and tooth positioner with conventional treatment," *Am. J. Orthod. Oral. Surg.* 1946, 32:285–293.

Kleeman et al., "The speed positioner," *J. Clin. Orthod.* 1996, 30:673–680.

Kuroda et al., "Three–dimensional dental cast analyzing system using laser scanning," *Am. J. Orthod. Dentofac. Orthop.* 1996, 110:365–369.

Nishiyama et al., "A new construction of tooth repositioner by LTV vinyl silicon rubber," *J. Nihon Univ. School of Dentistry* 1977, 19(2):93–102.

Nippon Dental Review, "New orthodontic device–dynamic positioner (D.P.)–I Approach to the proposal of D.P. and transparent silicone rubber," 1980, 452:61–74.

Nippon Dental Review, "New orthodontic device–dynamic positioner (D.P.)–II, Practice application and construction of D.P. and transparent silicone rubber," 1980, 454:107–130.

Nippon Dental Review, "New orthodontic device–dynamic positioner (D.P.)–III, Case reports of reversed occlusion," 457:146–164.

Nippon Dental Review, "New orthodontic device–dynamic positioner (D.P.)—Case reports of reversed occlusion," 1980, 458:112–129.

Raintree Essix & ARS Materials, Inc., Raintree Essix, Technical Magazine Table of contents and Essic Appliances, httpz://www.essix.com/magazine/dafault.html Aug. 13, 1997, 7 pages.

Shilliday, "Minimizing finishing problems with the mini–positioner," *Am. J. Orthod.* 1971, 59:596–599.

Warunek et al., "Physical and mechanical properties of elastomers in orthodontic positioners," *Am. J. Orthod. Dentofac. Orthop.* 1989, 95:388–400.

Wells, "Application of the positioner appliance in orthodontic treatment," *Am. J. Orthodont.* 1970, 58:351–366.

Lawrence F. Andrews, D.D.S., "The six to normal occlusion," *Am. J. Orthodont.* Sep. 1972, 296,308.

Lawrence F. Andrews, D.D.S., "Straight Wire, The Concept and Appliance," The Six Keys to Optimal Occlusion, 15–24.

Kamada et al., "Construction of Tooth Positioners with LTV Vinyl Silicone Rubber and Some Case Reports," *J. Nihon Univ. School of Dentistry*, Mar. 1982, 24(1):1–26.

Schroeder et al., "Algorithms I," The Visualization Toolkit chapter 6–9.9, 1996.

Proffit et al., "The First Stage of Comprehensive Treatment: Alignment and Leveling," Contemporary Orthodontics, Chapter 15, 470–533.

Warunek et al., "Clinical Use of Silicone Elastomer Appliances," *JCO* Oct. 1989, 694–700.

* cited by examiner

SYSTEMS AND METHODS FOR DENTAL TREATMENT PLANNING

CROSS-REFERENCES TO RELATED APPLICATIONS

This application claims priority from Provisional Application Serial No. 60/199,610, filed Apr. 25, 2000, and is a continuation-in-part of Application Ser. No. 09/313,289, filed May 13, 1999, the full disclosures of which are incorporated herein by reference.

BACKGROUND OF THE INVENTION

1. Field of the Invention

The invention relates generally to the field of orthodontics and, more particularly, to computer-automated development of an orthodontic treatment plan and appliance.

Repositioning teeth for aesthetic or other reasons is accomplished conventionally by wearing what are commonly referred to as "braces." Braces comprise a variety of appliances such as brackets, archwires, ligatures, and O-rings. Attaching the appliances to a patient's teeth is a tedious and time-consuming enterprise requiring many meetings with the treating orthodontist. Consequently, conventional orthodontic treatment limits an orthodontist's patient capacity and makes orthodontic treatment quite expensive. As such, the use of conventional braces is a tedious and time consuming process and requires many visits to the orthodontist's office. Moreover, from the patient's perspective, the use of braces is unsightly, uncomfortable, presents a risk of infection, and makes brushing, flossing, and other dental hygiene procedures difficult.

2. Description of the Background Art

Tooth positioners for finishing orthodontic treatment are described by Kesling in the *Am. J Orthod. Oral. Surg.* 31:297–304 (1945) and 32:285–293 (1946). The use of silicone positioners for the comprehensive orthodontic realignment of a patient's teeth is described in Warunek et al. (1989) *J. Clin. Orthod.* 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J Clin. Orthodon.* 30:673–680; Cureton (1996) *J Clin. Orthodon.* 30:390–395; Chiappone (1980) *J Clin. Orthodon.* 14:121–133; Shilliday (1971) *Am. J Orthodontics* 59:596–599; Wells (1970) *Am. J Orthodontics* 58:351–366; and Cottingham (1969) *Am. J. Orthodontics* 55:23–31.

Kuroda et al. (1996) *Am. J Orthodontics* 110:365–369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

BRIEF SUMMARY OF THE INVENTION

In one aspect, computer-implemented systems and methods implement a dental treatment plan by specifying tooth movement patterns using a two-dimensional array; and generating treatment paths to move the teeth in accordance with the specified pattern.

Implementations of the invention include one or more of the following. One dimension of the array identifies each stage in the teeth movement and one dimension of the array identifies a unique tooth. Tooth movement is specified by indicating a start stage and an end stage for a tooth. One or more tooth paths is determined based on the selected tooth movement pattern. The method includes selecting one or more clinical treatment prescriptions that include at least one of the following: space closure, reproximation, dental expansion, flaring, distalization, and lower incisor extraction. An appliance is fabricated for each treatment stage. The appliance can be either a removable appliance or a fixed appliance. The method also includes generating a three-dimensional model for the teeth for each treatment stage.

The system can conform to one or more constraints. The constraints relates to teeth crowding, teeth spacing, teeth extraction, teeth stripping, teeth rotation, and teeth movement. The teeth can be rotated approximately five and ten degrees (per stage) and can be incrementally moved in one or more stages (per stage), each stage moving each tooth approximately 0.2 mm to approximately 0.4 mm. The constraints can be stored in an array with one dimension of the array identifying each stage in the teeth movement. The treatment paths can include determining the minimum amount of transformation required to move each tooth from the initial position to the final position and creating each treatment path to require only the minimum amount of movement. Additionally, intermediate positions can be generated for at least one tooth between which the tooth undergoes translational movements of equal sizes. Further, intermediate positions can be generated for at least one tooth between which the tooth undergoes translational movements of unequal sizes. A set of rules can be applied to detect any collisions that will occur as the patient's teeth move along the treatment paths. Collisions can be detected by calculating distances between a first tooth and a second tooth by establishing a neutral projection plane between the first tooth and the second tooth, establishing a z-axis that is normal to the plane and that has a positive direction and a negative direction from each of a set of base points on the projection plane, computing a pair of signed distances comprising a first signed distance to the first tooth and a second signed distance to the second tooth, the signed distances being measured on a line through the base points and parallel to the z-axis, and determining that a collision occurs if any of the pair of signed distances indicates a collision. Where the positive direction for the first distance is opposite the positive direction for the second distance, a collision is detected if the sum of any pair of signed distances is less than or equal to zero. Information indicating whether the patient's teeth are following the treatment paths can be used to revise the treatment paths. More than one candidate treatment path for each tooth can be generated and graphically displayed for each candidate treatment path to a human user for selection. A set of rules can be applied to detect any collisions that will occur as the patient's teeth move along the treatment paths. Collisions can be detected by calculating distances between a first tooth and a second tooth by: establishing a neutral projection plane between the first tooth and the second tooth, establishing a z-axis that is normal to the plane and that has a positive direction and a negative direction from each of a set of base points on the projection plane, computing a pair of signed distances comprising a first signed distance to the first tooth and a second signed distance to the second tooth, the signed distances being measured on a line through the base points and parallel to the z-axis, and determining that a collision occurs if any of the pair of signed distances indicates a collision. A collision can also be detected if the sum of any pair of signed distances is less than or equal to zero. A set of rules can be applied to detect any improper bite occlusions that will occur as the patient's teeth move along the treatment paths. A value for a malocclusion index can be computed and the value displayed to a human user. The treatment paths can be generated by receiving data indicating restraints on movement of the patient's teeth and applying the data to generate the treatment paths. A three-dimensional (3D) graphical representation of the teeth at the positions corresponding to a selected data set can be rendered. The graphical representation of the teeth to provide a visual display of the movement of the teeth along the treatment paths can be generated. A graphical interface, with components representing the control buttons on a videocassette recorder, which a human user can manipulate to control the animation, can be generated. A portion of the data in the selected data set may be used to render the graphical representation of the teeth. A level-of-detail compression can be applied to the data set to render the graphical representation of the teeth. A human user can modify the graphical representation of the teeth and the selected data set can be modified in response to the user's request. A human user can select a tooth in the graphical representation and, in response, information about the tooth can be displayed. The information can relate to the motion that the tooth will experience while moving along the treatment path. The information can also indicate a linear distance between the tooth and another tooth selected in the graphical representation. The teeth can be rendered at a selected one of multiple viewing orthodontic-specific viewing angles. A user interface through which a human user can provide text-based comments after viewing the graphical representation of the patient's teeth can be provided. The graphical representation data can be downloaded to a remote computer at which a human view wishes to view the graphical representation. An input signal from a 3D gyroscopic input device controlled by a human user can be applied to alter the orientation of the teeth in the graphical representation.

DETAILED DESCRIPTION OF THE INVENTION

Figure 1:
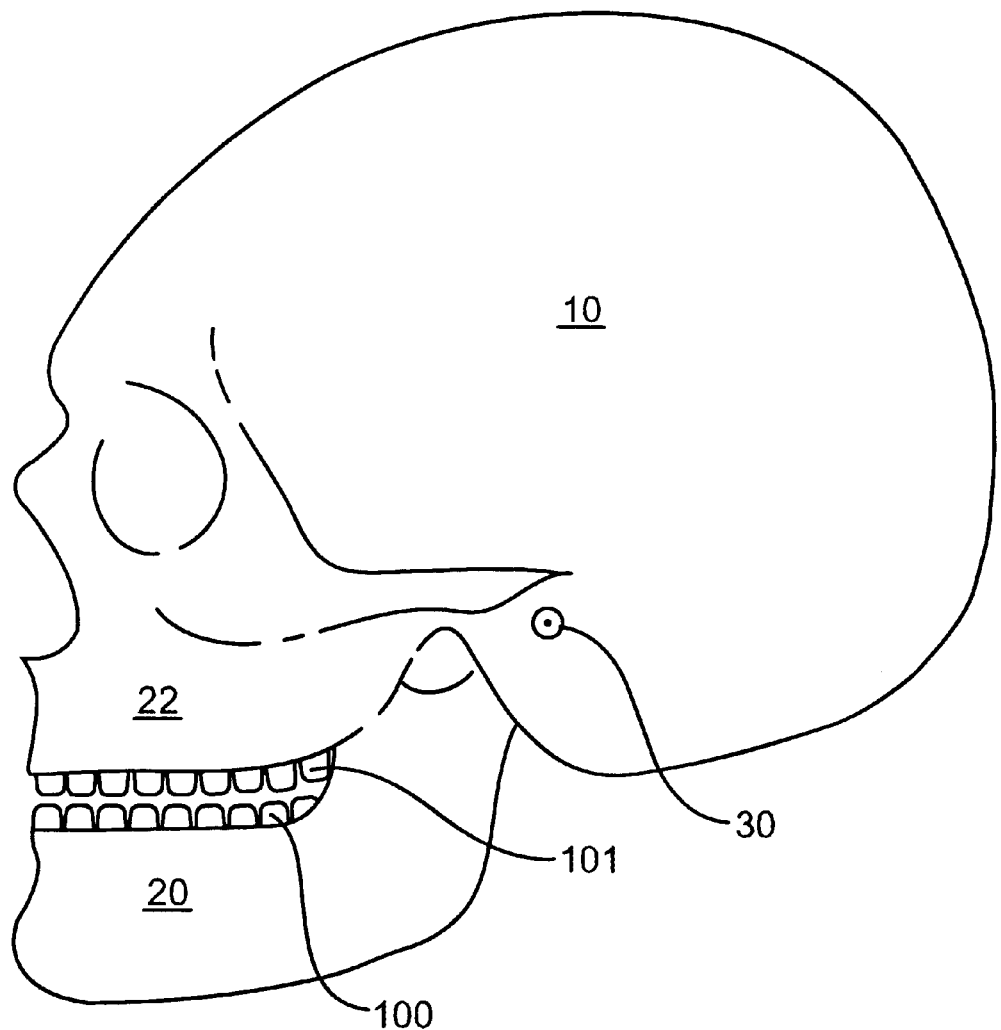
FIG. 1 is an elevational diagram showing the anatomical relationship of the jaws of a patient.

FIG. 1 shows a skull 10 with an upper jawbone 22 and a lower jawbone 20. The lower jawbone 20 hinges at a joint 30 to the skull 10. The joint 30 is called a temporomandibular joint (TMJ). The upper jawbone 22 is associated with an upper jaw 101, while the lower jawbone 20 is associated with a lower jaw 100.

A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements which are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
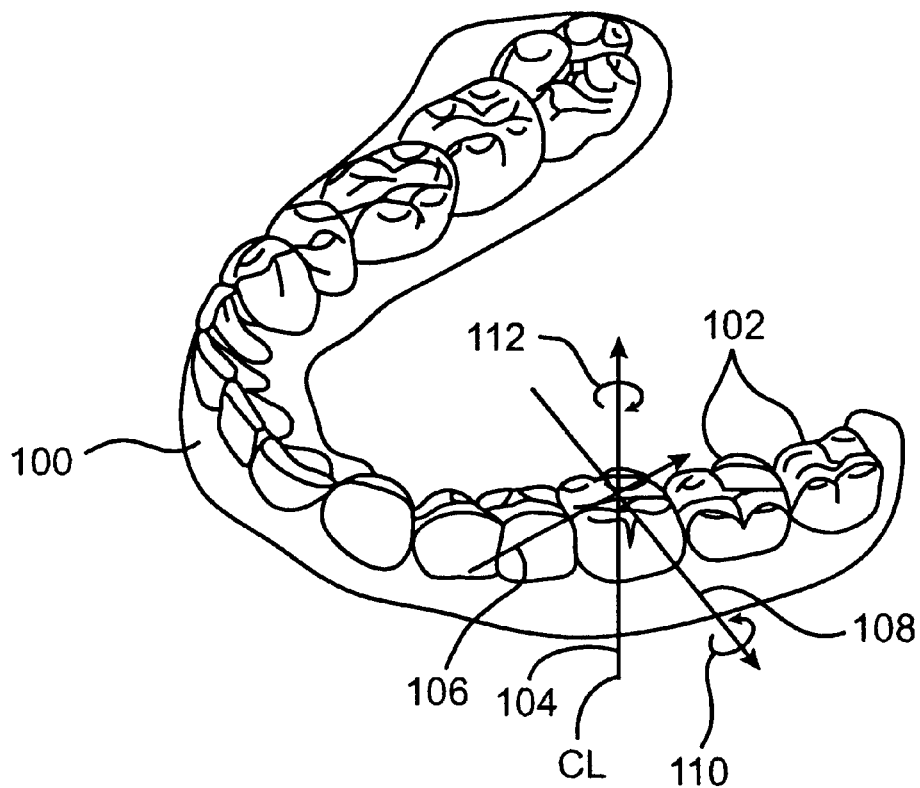
FIG. 2A illustrates in more detail the patient's lower jaw and provides a general indication of how teeth may be moved by the methods and apparatus of the present invention.

Referring now to FIG. 2A, the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 114. Thus, all possible free-form motions of the tooth can be performed.

Figure 2B:
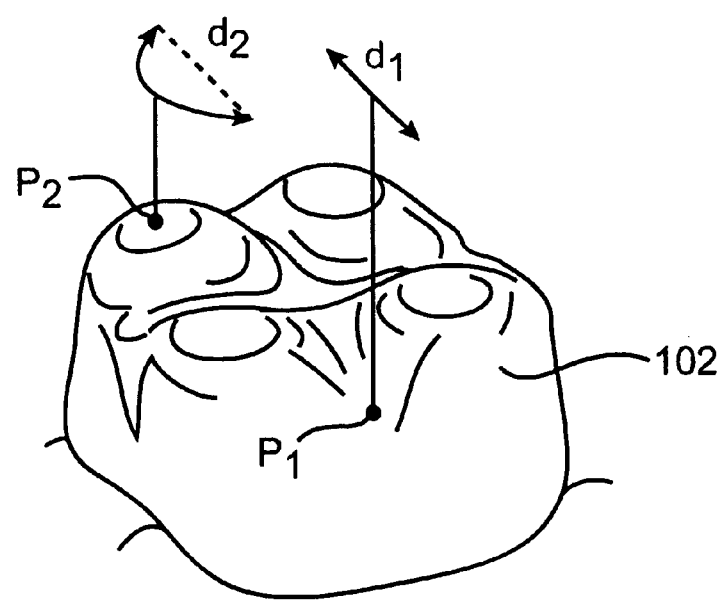
FIG. 2B illustrates a single tooth from FIG. 2A and defines how tooth movement distances are determined.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth which undergoes the maximum movement for that tooth in any treatment step.

Figure 2C:
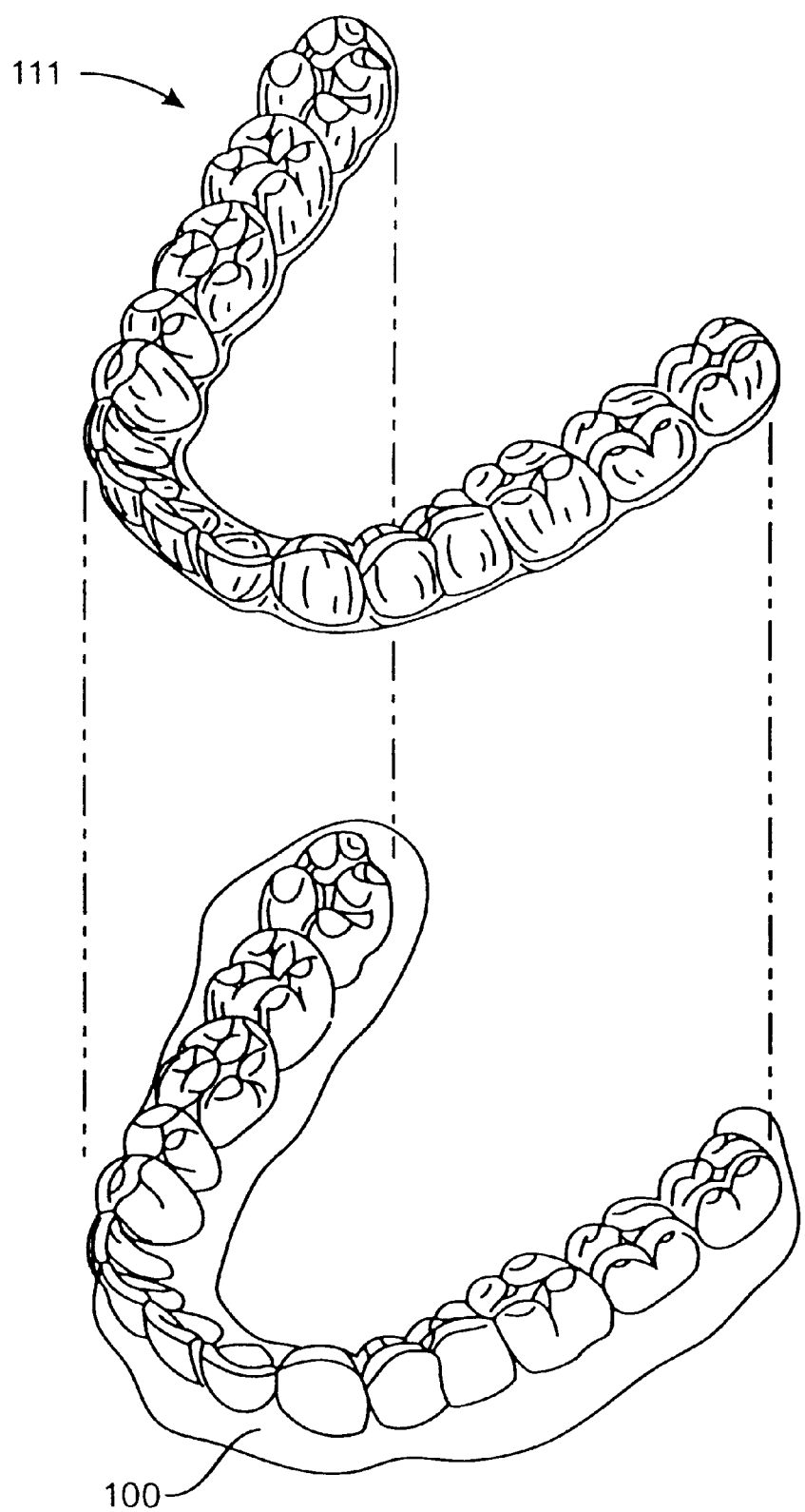
FIG. 2C illustrates the jaw of FIG. 2A together with an incremental position adjustment appliance which has been configured according to the methods and apparatus of the present invention.

FIG. 2C shows one adjustment appliance 111 which is worn by the patient in order to achieve an incremental repositioning of individual teeth in the jaw as described generally above. The appliance is a polymeric shell having a teeth receiving cavity. This is described in U.S. application Ser. No. 09/169,036, filed Oct. 8, 1998, which claims priority from U.S. application Ser. No. 08/947,080, filed Oct. 8, 1997, which in turn claims priority from provisional application number 06/050,352, filed Jun. 20, 1997 (collectively the "prior applications"), the full disclosures of which are incorporated by reference.

As set forth in the prior applications, each polymeric shell may be configured so that its tooth receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliance remains. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such overcorrection may be desirable in order to offset potential relapse after the repositioning method has been terminated, i.e., to permit some movement of individual teeth back toward their precorrected positions. Overcorrection may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the teeth which are moved can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth which would not be possible in the absence of such an anchor.

Figure 3:
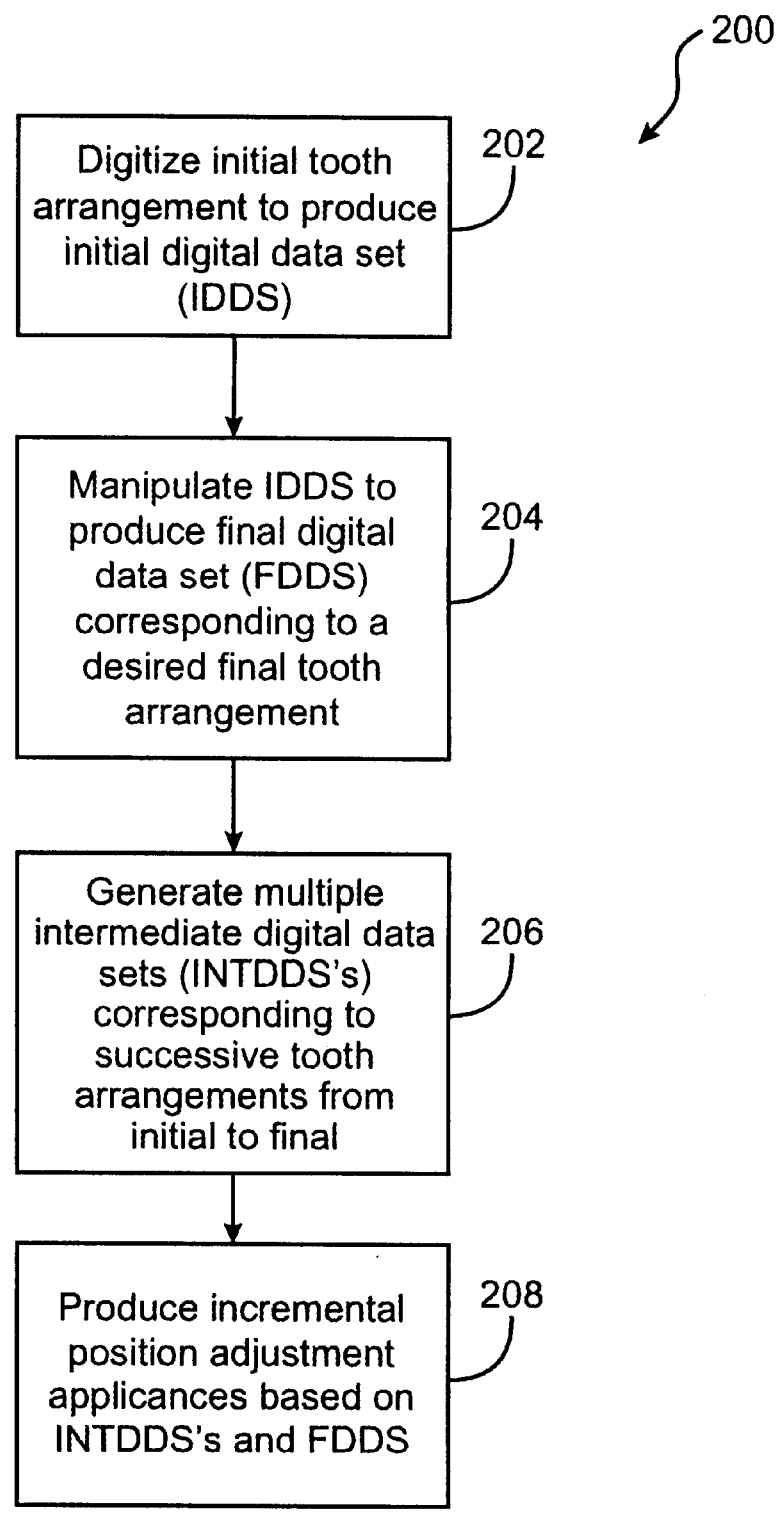
FIG. 3 is a block diagram illustrating a process for producing incremental position adjustment appliances.

FIG. 3 shows a process 200 for producing the incremental position adjustment appliances for subsequent use by a patient to reposition the patient's teeth. As a first step, an initial digital data set (IDDS) representing an initial tooth arrangement is obtained (step 202).

In some implementations, the IDDS includes data obtained by scanning a physical model of the patient's teeth, such as by scanning a positive impression or a negative impression of the patient's teeth with a laser scanner or a destructive scanner. The positive and negative impression may be scanned while interlocked with each other to provide more accurate data. The initial digital data set also may include volume image data of the patient's teeth, which the computer can convert into a 3D geometric model of the tooth surfaces, for example using a conventional marching cubes technique. In some embodiments, the individual tooth models include data representing hidden tooth surfaces, such as roots imaged through x-ray, CT scan, or MRI techniques. Tooth roots and hidden surfaces also can be extrapolated from the visible surfaces of the patient's teeth. The IDDS is then manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204).

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement which is customized to the patient's teeth, as discussed below. After applying the ideal model to the computer representation, and the position of the teeth is optimized to fit the ideal model. The ideal model may be specified by one or more arch forms, or may be specified using various features associated with the teeth.

The FDDS is created by following the orthodontists' prescription to move the teeth in the model to their final positions. In one embodiment, the prescription is entered into a computer, which automatically computes the final positions of the teeth. In alternative other embodiments, a user moves the teeth into their final positions by independently manipulating one or more teeth while satisfying the constraints of the prescription. Various combinations of the above described techniques may also be used to arrive at the final tooth positions.

One method for creating the FDDS involves moving the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDs and the FDDS (step 208).

After the teeth and other components have been placed or removed to produce a model of the final tooth arrangement, it is necessary to generate a treatment plan which produces a series of INTDDS's and FDDS as described previously. To produce these data sets, it is necessary to define or map the movement of selected individual teeth from the initial position to the final position over a series of successive steps. In addition, it may be necessary to add other features to the data sets in order to produce desired features in the treatment appliances. For example, it may be desirable to add wax patches to the image in order to define cavities or recesses for particular purposes, such as to maintain a space between the appliance and particular regions of the teeth or jaw in order to reduce soreness of the gums, avoid periodontal problems, allow for a cap, and the like. Additionally, it will often be necessary to provide a receptacle or aperture intended to accommodate an anchor which is to be placed on a tooth in order to permit the tooth to be manipulated in a manner that requires the anchor, e.g., to be lifted relative to the jaw.

In the manner discussed above, information on how the patient's teeth should move from an initial, untreated state to a final, treated state is used to generate a prescription, or treatment plan. The prescription takes into consideration the following:

1. Initial Position: a detailed description of the initial maloclussion.
2. Final Position: a detailed description of treatment goals for the patient.
3. Movement: a detailed, sequential description of how the patient's teeth should be moved in order to accomplish the desired goals for final placement.

1. Initial Position
   The initial position section describes in detail the patient's malocclusion.
   Considerations Include
   a. Crowding
   b. Spacing
   c. Extraction
   d. Stripping
   Additionally, considerations for the Final Position discussed below may also be used.
2. Final Position
   This section is a detailed description of your final position objectives and treatment goals—both static and functional. These considerations include
   a. Overjet
   b. Overbite
   c. Midlines
   d. Functional Occlusion
   e. Classification
   f. Torque
   g. Tip
   h. Rotations
   i. Lingual/Palatal
   j. Buccal/Facial
   k. Intercuspation
   l. Initial Position of the Occlusion—CR/CO Considerations
   m. Interarch Issues
   n. Intra-arch Issues
   o. Space
3. Movement
   The movement section specifies an order in moving the patient's teeth in order to achieve the goals for final placement. In this process, the orthodontist has precise control over which teeth the orthodontist wants to move and which teeth to anchor (not move), thereby breaking the treatment down into discrete stages. The movement order information is captured for both the upper and the lower arches.

At each stage, major and minor tooth movements are analyzed. Major movements usually occur at the beginning of a tooth's movement. Minor movements usually occur as "detailing" movements that occur toward the end of treatment. On average, each aligner should be able to accomplish move about 0.25–0.33 mm and to rotate about 5–10 degrees within a 2-week period. However, biologic variability, patient and clinician preferences are also taken into consideration. Additionally, various movements such as distalization, tip, and torque can have separate parameters.

Figure 4:
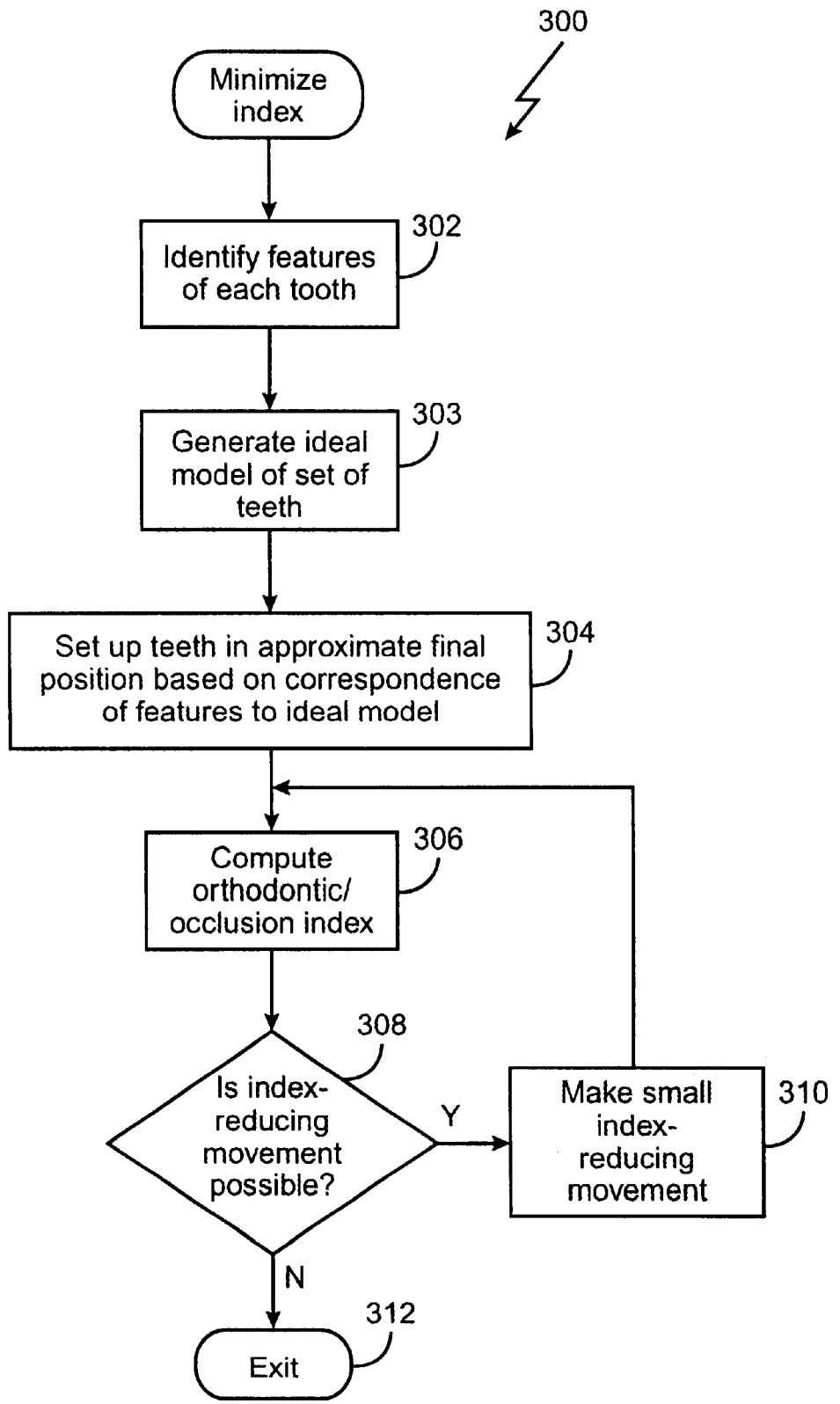
FIG. 4 is a flow chart illustrating a process for optimizing a final placement of the patient's teeth.

Based on these considerations, a plan is generated for moving teeth. FIG. 4 illustrates a process 300 for generating tooth movements while minimizing teeth indices, as discussed in copending U.S. application Ser. No. 09/169,034, the content of which is hereby incorporated by reference. First, the process 300 automatically or, with human assistance, identifies various features associated with each tooth to arrive at a model of the teeth (step 302). An ideal model set of teeth is then generated either from casts of the patient's teeth or from patients with a known acceptable occlusion (step 303).

From step 302, the process 300 positions the model of the teeth in its approximate final position based on a correspondence of features to the ideal model (step 304). In that step, each tooth model is moved so that its features are aligned to the features of a corresponding tooth in the ideal model. The features may be based on cusps, fossae, ridges, distance-based metrics, or shape-based metrics. Shape-based metrics may be expressed as a function of the patient's arches, among others.

Next, the process 300 computes an orthodontic/occlusion index (step 306). One index which may be used is the PAR (Peer Assessment Rating) index. In addition to PAR, other metrics such as shape-based metrics or distance-based metrics may be used. The PAR index identifies how far a tooth is from a good occlusion. A score is assigned to various occlusal traits which make up a malocclusion. The individual scores are summed to obtain an overall total, representing the degree a case deviates from normal alignment and occlusion. Normal occlusion and alignment is defined as all anatomical contact points being adjacent, with a good intercuspal mesh between upper and lower buccal teeth, and with nonexcessive overjet and overbite.

In PAR, a score of zero would indicate good alignment, and higher scores would indicate increased levels of irregularity. The overall score is recorded on pre- and posttreatment dental casts. The difference between these scores represents the degree of improvement as a result of orthodontic intervention and active treatment. The eleven components of the PAR Index are: upper right segment; upper anterior segment; upper left segment; lower right segment; lower anterior segment; lower left segment; right buccal occlusion; overjet; overbite; centerline; and left buccal occlusion. In addition to the PAR index, other indices may be based on distances of the features on the tooth from their ideal positions or ideal shapes.

From step 306, the process 300 determines whether additional index-reducing movements are possible (step 308). Here, all possible movements are attempted, including small movements along each major axis as well as small movements with minor rotations. An index value is computed after each small movement and the movement with the best result is selected. In this context, the best result is the result that minimizes one or more metrics such as PAR-based metrics, shape-based metrics or distance-based metrics. The optimization may use a number of techniques, including simulated annealing technique, hill climbing technique, best-first technique, Powell method, and heuristics technique, among others. Simulated annealing techniques may be used where the index is temporarily increased so that another path in the search space with a lower minimum may be found. However, by starting with the teeth in an almost ideal position, any decrease in the index should converge to the best result.

In step 308, if the index can be optimized by moving the tooth, incremental index-reducing movement inputs are added (step 310) and the process loops back to step 306 to continue computing the orthodontic/occlusion index. Alternatively, in the event that the index cannot be further optimized, the process 300 exits (step 312).

In generating the index reducing movements of step 310, the process considers a set of movement constraints which affect the tooth path movement plan. In one embodiment, movement information for about fifty discrete stages is specified. Each stage represents a single aligner, which is expected to be replaced about every two weeks. Thus, each stage represents about a two-week period. In one embodiment, a two-dimensional array is used to track specific movements for each tooth at a specific period of time. One dimension of this array relates to teeth identification, while the second dimension relates to the time periods or stages. Considerations on when a tooth may be moved include the following:

a. Mesial
b. Distal
c. Buccal/Facial
d. Lingual/Palatial
e. Expansion
f. Space
g. Teeth moving past each other
h. Intrusion
i. Extrusion
j. Rotations
k. Which teeth are moving when?
l. Which teeth move first?
m. Which teeth need to be moved before others are moved?
n. What movements are easily done?
o. Anchorage
p. The orthodontist user's philosophy on distalization of molars and minor expansion in adults In one embodiment, the user can change the number of desired treatment stages from the initial to the target states of the teeth. Any component that is not moved is assumed to remain stationary, and thus its final position is assumed to be the same as the initial position (likewise for all intermediate positions, unless one or more key frames are defined for that component).

The user may also specify "key frames" by selecting an intermediate state and making changes to component position(s). In some embodiments, unless instructed otherwise, the software automatically linearly interpolates between all user-specified positions (including the initial position, all key frame positions, and the target position). For example, if only a final position is defined for a particular component, each subsequent stage after the initial stage will simply show the component an equal linear distance and rotation (specified by a quaternion) closer to the final position. If the user specifies two key frames for that component, the component will "move" linearly from the initial position through different stages to the position defined by the first key frame. It will then move, possibly in a different direction, linearly to the position defined by the second key frame. Finally, it will move, possibly in yet a different direction, linearly to the target position.

These operations may be done independently to each component, so that a key frame for one component will not affect another component, unless the other component is also moved by the user in that key frame. One component may accelerate along a curve between one pair of stages (e.g., stages 3 and 8 in a treatment plan having that many stages), while another moves linearly between another pair of stages (e.g., stages 1 to 5), and then changes direction suddenly and slows down along a linear path to a later stage (e.g., stage 10). This flexibility allows a great deal of freedom in planning a patient's treatment.

In some implementations, non-linear interpolation is used instead of or in addition to linear interpolation to construct a treatment path among key frames. In general, a non-linear path, such as a spline curve, created to fit among selected points is shorter than a path formed from straight line segments connecting the points. A "treatment path" describes the transformation curve applied to a particular tooth to move the tooth from its initial position to its final position. A typical treatment path includes some combination of rotational and translational movement of the corresponding tooth, as described above.

Figure 5:
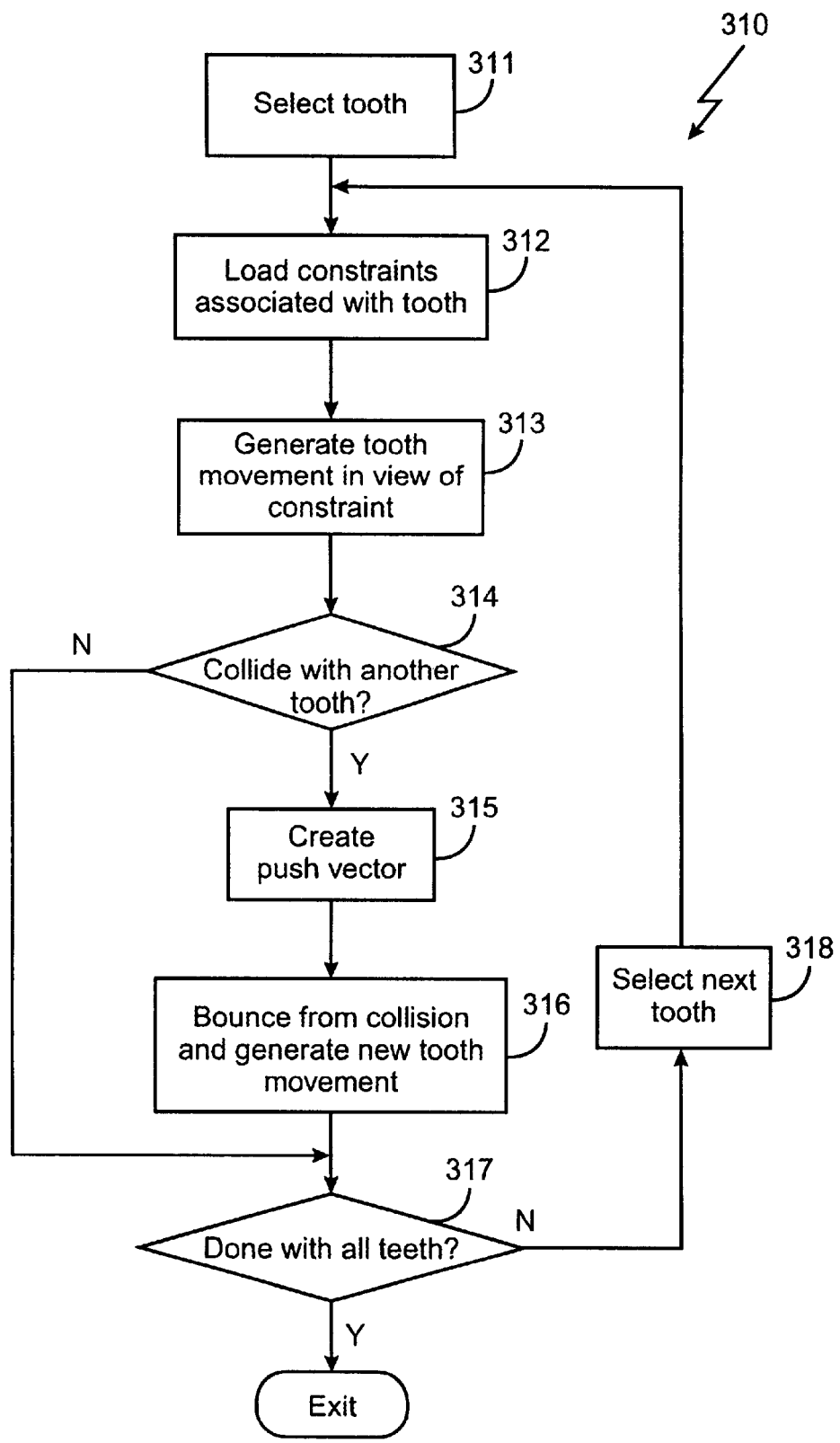
FIG. 5 is a flow chart illustrating the positioning of teeth at various steps of an orthodontic treatment plan.

FIG. 5 shows step 310 in more detail. Initially, a first tooth is selected (step 311). Next, constraints associated with the tooth is retrieved for the current stage or period (step 312). Thus, for the embodiment which keeps a two-dimensional array to track specific movements for each tooth at a specific period of time, the tooth identification and the time period or stage information are used to index into the array to retrieve the constraints associated with the current tooth.

Next, a tooth movement plan which takes into consideration the constraints is generated (step 313). The process of FIG. 5 then detects whether the planned movements would cause collisions with neighboring teeth (step 314). The collision detection process determines if any of the geometries describing the tooth surfaces intersect. If there are no obstructions, the space is considered free; otherwise it is obstructed. Suitable collision detection algorithms are discussed in more detail below.

If a collision occurs, a "push" vector is created to shift the path of the planned movement (step 315). Based on the push vector, the current tooth "bounces" from the collision and a new tooth movement is generated (step 316). From step 314 or 316, the movement of the current tooth is finalized.

Next, the process of FIG. 5 determines whether tooth movement plans have been generated for all teeth (step 317), and if so, the process exits. Alternatively, the next tooth in the treatment plan is selected (318), and the process of FIG. 5 loops back to step 312 to continue generating tooth movement plans.

Figure 6:
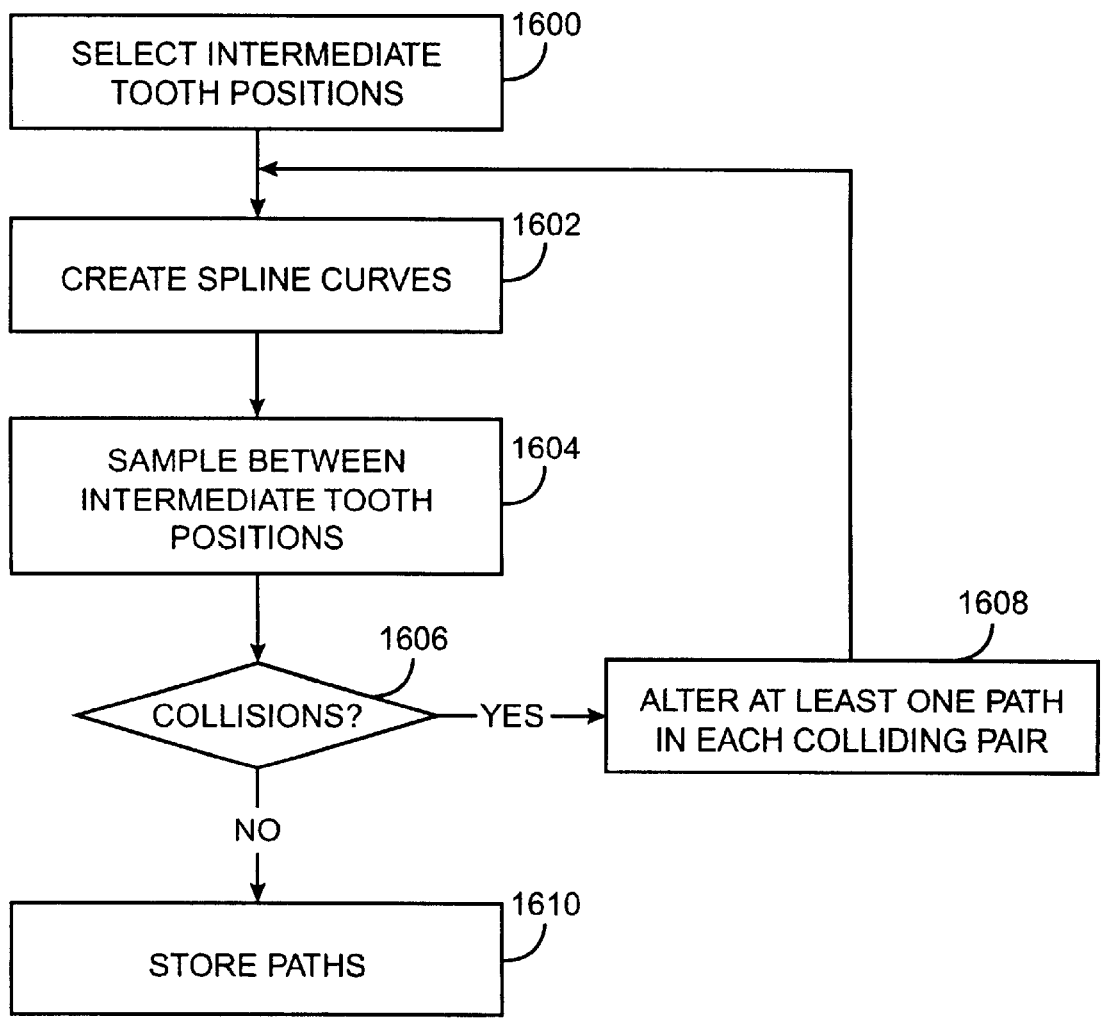
FIG. 6 is a flow chart of a process for determining a tooth's path among intermediate positions during an orthodontic treatment plan.

The resulting final path consists of a series of vectors, each of which represents a group of values of the interpolation parameters of the translational and rotational components of the transformations of the moving teeth. Taken together, these constitute a schedule of tooth movement which avoids tooth-to-tooth interferences. Pseudo code for generating the tooth path in view of specified constraints is shown below:

For each tooth path model
  For each path increment
    Load constrains associated with each tooth
    Move the tooth in view of constraint
    Perform tooth collision detection
    If collision occurs, for associated colliding teeth create "push" vector and "bounce" back from collision to avoid collision
  end for
end tooth path model FIG. 6 is a flow chart of a computer-implemented process for generating non-linear treatment paths along which a patient's teeth will travel during treatment. The non-linear paths usually are generated automatically by computer program, in some cases with human assistance. The program receives as input the initial and final positions of the patient's teeth and uses this information to select intermediate positions for each tooth to be moved (step 1600). The program then applies a conventional spline curve calculation algorithm to create a spline curve connecting each tooth's initial position to the tooth's final position (step 1602). In many situations, the curve is constrained to follow the shortest path between the intermediate positions. The program then samples each spline curve between the intermediate positions (step 1604) and applies the collision detection algorithm to the samples (step 1606). If any collisions are detected, the program alters the path of at least one tooth in each colliding pair by selecting a new position for one of the intermediate steps (step 1608) and creating a new spline curve (1602). The program then samples the new path (1604) and again applies the collision detection algorithm (1606). The program continues in this manner until no collisions are detected. The routine then stores the paths, e.g., by saving the coordinates of each point in the tooth at each position on the path in an electronic storage device, such as a hard disk (step 1610).

The path-generating program, whether using linear or non-linear interpolation, selects the treatment positions so that the tooth's treatment path has approximately equal lengths between each adjacent pair of treatment steps. The program also avoids treatment positions that force portions of a tooth to move with more than a given maximum velocity. For example, a tooth can be scheduled to move along a first path T1 from an initial position T11 to a final position T13 through an intermediate position T12, which lies closer to the final position T13. Another tooth is scheduled to move along a shorter path T2 from an initial position T21 to a final position T23 through an intermediate position T22, which is equidistant from the initial and final positions T21, T23. In this situation, the program may choose to insert a second intermediate position T14 along the first path T1 that is approximately equidistant from the initial position T11 and the intermediate position T12 and that is separated from these two positions by approximately the same distance that separates the intermediate position T12 from the final position T13. Altering the first path T1 in this manner ensures that the first tooth will move in steps of equal size. However, altering the first path T1 also introduces an additional treatment step having no counterpart in the second path T2. The program can respond to this situation in a variety of ways, such as by allowing the second tooth to remain stationary during the second treatment step (i.e., as the first tooth moves from one intermediate position T14 to the other intermediate position T13) or by altering the second path T2 to include four equidistant treatment positions. The program determines how to respond by applying a set of orthodontic constraints that restrict the movement of the teeth.

Orthodontic constraints that may be applied by the path-generating program include the minimum and maximum distances allowed between adjacent teeth at any given time, the maximum linear or rotational velocity at which a tooth should move, the maximum distance over which a tooth should move between treatment steps, the shapes of the teeth, the characteristics of the tissue and bone surrounding the teeth (e.g., ankylose teeth cannot move at all), and the characteristics of the aligner material (e.g., the maximum distance that the aligner can move a given tooth over a given period of time). For example, the patient's age and jawbone density may dictate certain "safe limits" beyond which the patient's teeth should not forced to move. In general, a gap between two adjacent, relatively vertical and nontipped central and lateral teeth should not close by more than about 1 mm every seven weeks. The material properties of the orthodontic appliance also limit the amount by which the appliance can move a tooth. For example, conventional retainer materials usually limit individual tooth movement to approximately 0.5 mm between treatment steps. The constraints have default values that apply unless patient-specific values are calculated or provided by a user. Constraint information is available from a variety of sources, including text books and treating clinicians.

In selecting the intermediate positions for each tooth, the path-generating program invokes the collision detection program to determine whether collisions will occur along the chosen paths. The program also inspects the patient's occlusion at each treatment step along the path to ensure that the teeth align to form an acceptable bite throughout the course of treatment. If collisions or an unacceptable bite will occur, or if a required constraint cannot be satisfied, the program iteratively alters the offending tooth path until all conditions are met. The virtual articulator described above is one tool for testing bite occlusion of the intermediate treatment positions.

Figure 7:
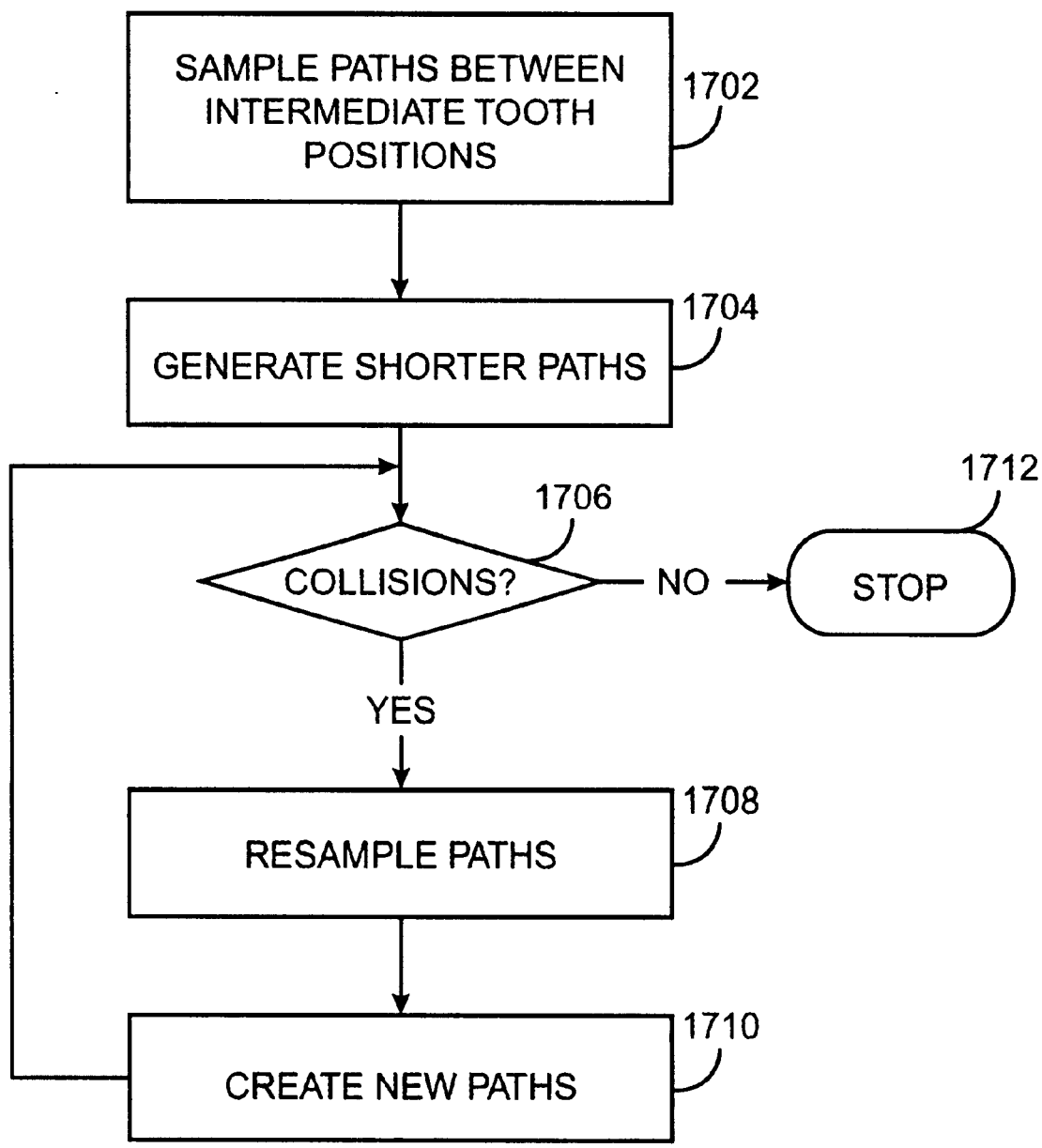
FIG. 7 is a flow chart of a process for optimizing the path of a tooth from an initial position to a final position during an orthodontic treatment plan.

As shown in FIG. 7, once the path-generating program has established collision-free paths for each tooth to be moved, the program calls an optimization routine that attempts to make the transformation curve for each tooth between the initial and final positions more linear. The routine begins by sampling each treatment path at points between treatment steps (step 1702), e.g., by placing two sample points between each treatment step, and calculating for each tooth a more linear treatment path that fits among the sample points (step 1704). The routine then applies the collision detection algorithm to determine whether collisions result from the altered paths (step 1706). If so, the routine resamples the altered paths (step 1708) and then constructs for each tooth an alternative path among the samples (step 1710). The routine continues in this manner until no collisions occur (step 1712).

In some embodiments, as alluded to above, the software automatically computes the treatment path, based upon the IDDS and the FDDS. This is accomplished using a path scheduling algorithm which determines the rate at which each component, i.e., each tooth, moves along the path from the initial position to the final position. The path scheduling algorithm determines the treatment path while avoiding "round-tripping," i.e., while avoiding moving a tooth along a distance greater than absolutely necessary to straighten the teeth. Such motion is highly undesirable, and has potential negative effects on the patient.

One implementation of the path scheduling algorithm attempts first to schedule or stage the movements of the teeth by constraining each tooth to the most linear treatment path between the initial and final positions. The algorithm then resorts to less direct routes to the final positions only if collisions will occur between teeth along the linear paths or if mandatory constraints will be violated. The algorithm applies one of the path-generation processes described above, if necessary, to construct a path for which the intermediate treatment steps do not lie along a linear transformation curve between the initial and final positions. Alternatively, the algorithm schedules treatment paths by drawing upon a database of preferred treatments for exemplary tooth arrangements. This database can be constructed over time by observing various courses of treatment and identifying the treatment plans that prove most successful with each general class of initial tooth arrangements. The path scheduling algorithm can create several alternative paths and present each path graphically to the user. The algorithm provides as output the path selected by the user.

In other implementations, the path scheduling algorithm utilizes a stochastic search technique to find an unobstructed path through a configuration space which describes possible treatment plans. One approach to scheduling motion between two user defined global key frames is described below. Scheduling over a time interval which includes intermediate key frames is accomplished by dividing the time interval into subintervals which do not include intermediate key frames, scheduling each of these intervals independently, and then concatenating the resulting schedules.

A collision or interference detection algorithm employed in one embodiment is based on the algorithm described in SIGGRAPH article, Stefan Gottschalk et al. (1996): "OBBTree: A Hierarchical Structure for Rapid Interference Detection." The contents of the SIGGRAPH article are herein incorporated by reference.

The algorithm is centered around a recursive subdivision of the space occupied by an object, which is organized in a binary-tree like fashion. Triangles are used to represent the teeth in the DDS. Each node of the tree is referred to as an oriented bounding box (OBB) and contains a subset of triangles appearing in the node's parent. The children of a parent node contain between them all of the triangle data stored in the parent node.

The bounding box of a node is oriented so it tightly fits around all of the triangles in that node. Leaf nodes in the tree ideally contain a single triangle, but can possibly contain more than one triangle. Detecting collisions between two objects involves determining if the OBB trees of the objects intersect. If the OBBs of the root nodes of the trees overlap, the root's children are checked for overlap. The algorithm proceeds in a recursive fashion until the leaf nodes are reached. At this point, a robust triangle intersection routine is used to determine if the triangles at the leaves are involved in a collision.

The collision detection technique described here provides several enhancements to the collision detection algorithm described in the SIGGRAPH article. For example, OBB trees can be built in a lazy fashion to save memory and time. This approach stems from the observation that some parts of the model will never be involved in a collision, and consequently the OBB tree for such parts of the model need not be computed. The OBB trees are expanded by splitting the internal nodes of the tree as necessary during the recursive collision determination algorithm.

Moreover, the triangles in the model which are not required for collision data may also be specifically excluded from consideration when building an OBB tree. For instance, motion may be viewed at two levels. Objects may be conceptualized as "moving" in a global sense, or they may be conceptualized as "moving" relative to other objects. The additional information improves the time taken for the collision detection by avoiding recomputation of collision information between objects which are at rest relative to each other since the state of the collision between such objects does not change.

Figure 8:
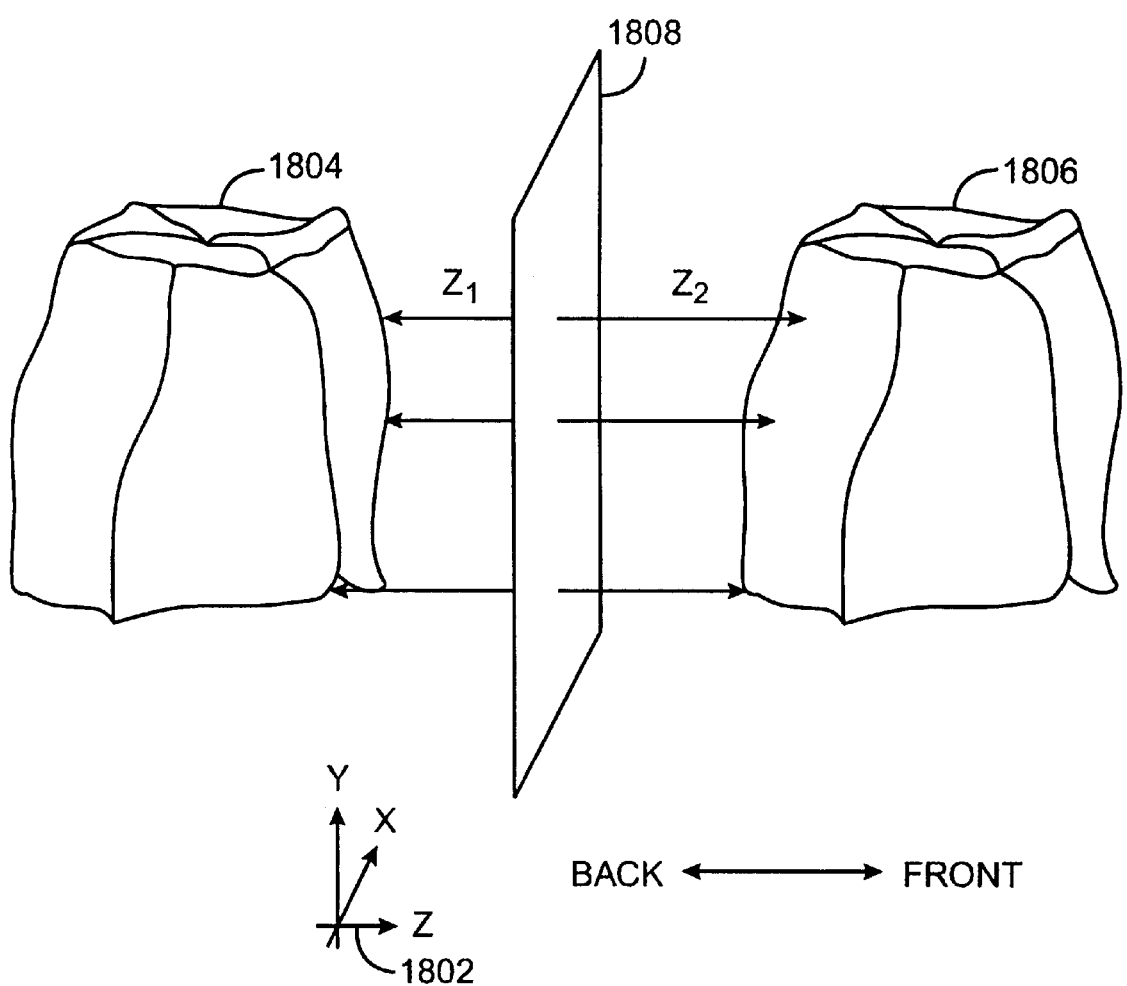
FIG. 8 is a diagram illustrating a buffering technique for use in a collision detection algorithm.

FIG. 8 illustrates an alternative collision detection scheme, one which calculates a "collision buffer" oriented along a z-axis 1802 along which two teeth 1804, 1806 lie. The collision buffer is calculated for each treatment step or at each position along a treatment path for which collision detection is required. To create the buffer, an x,y plane 1808 is defined between the teeth 1804, 1806. The plane must be "neutral" with respect to the two teeth. Ideally, the neutral plane is positioned so that it does not intersect either tooth. If intersection with one or both teeth is inevitable, the neutral plane is oriented such that the teeth lie, as much as possible, on opposite sides of the plane. In other words, the neutral plane minimizes the amount of each tooth's surface area that lies on the same side of the plane as the other tooth.

In the plane 1808 is a grid of discrete points, the resolution of which depends upon the required resolution for the collision detection routine. A typical high-resolution collision buffer includes a 400×400 grid; a typical low-resolution buffer includes a 20×20 grid. The z-axis 1802 is defined by a line normal to the plane 1808.

The relative positions of the teeth 1804, 1806 are determined by calculating, for each of the points in the grid, the linear distance parallel to the z-axis 1802 between the plane 1808 and the nearest surface of each tooth 1804, 1806. For example, at any given grid point (M,N), the plane 1808 and the nearest surface of the rear tooth 1804 are separated by a distance represented by the value Z1(M,N), while the plane 1808 and the nearest surface of the front tooth 1806 are separated by a distance represented by the value Z2(M,N). If the collision buffer is defined such that the plane 1808 lies at z=0 and positive values of z lie toward the back tooth 1804, then the teeth 1804, 1806 collide when Z1(M,N) Z2(M,N) at any grid point (M,N) on the plane 1808.

Figure 9:
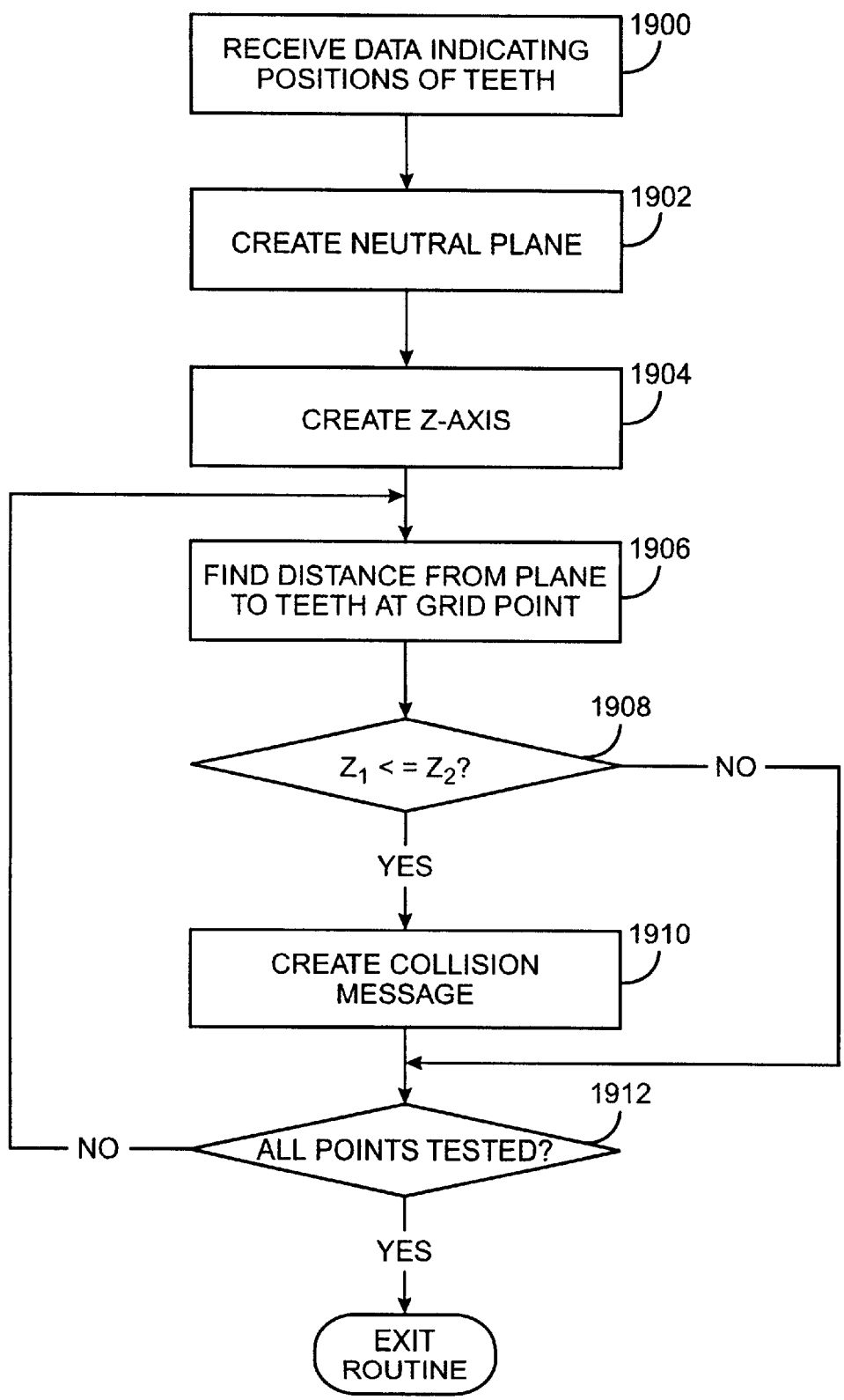
FIG. 9 is a flow chart for a collision detection technique.

FIG. 9 is a flow chart of a collision detection routine implementing this collision buffer scheme. The routine first receives data from one of the digital data sets indicating the positions of the surfaces of the teeth to be tested (step 1900). The routine then defines the neutral x,y-plane (step 1902) and creates the z-axis normal to the plane (step 1904).

The routine then determines for the x,y-position of the first grid point on the plane the linear distance in the z-direction between the plane and the nearest surface of each tooth (step 1906). To detect a collision at that x,y-position, the routine determines whether the z-position of the nearest surface of the rear tooth is less than or equal to the z-position of the nearest surface of the front tooth (step 1908). If so, the routine creates an error message, for display to a user or for feedback to the path-generating program, indicating that a collision will occur (step 1910). The routine then determines whether it has tested all x,y-positions associated with grid points on the plane (step 1912) and, if not, repeats the steps above for each remaining grid point. The collision detection routine is performed for each pair of adjacent teeth in the patient's mouth at each treatment step.

The system may also incorporate and the user may at any point use a "movie" feature to show an animation of the movement from initial to target states. This is helpful for visualizing overall component movement throughout the treatment process.

As described above, one suitable user interface for component identification is a three dimensional interactive graphical user interface (GUI). A three-dimensional GUI is also advantageous for component manipulation. Such an interface provides the treating professional or user with instant and visual interaction with the digital model components. The three-dimensional GUI provides advantages over interfaces that permit only simple low-level commands for directing the computer to manipulate a particular segment. In other words, a GUI adapted for manipulation is better in many ways than an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the data sets which can comprise text and/or the sequence number of the apparatus. The annotation is added as recessed text (i.e., it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 10:
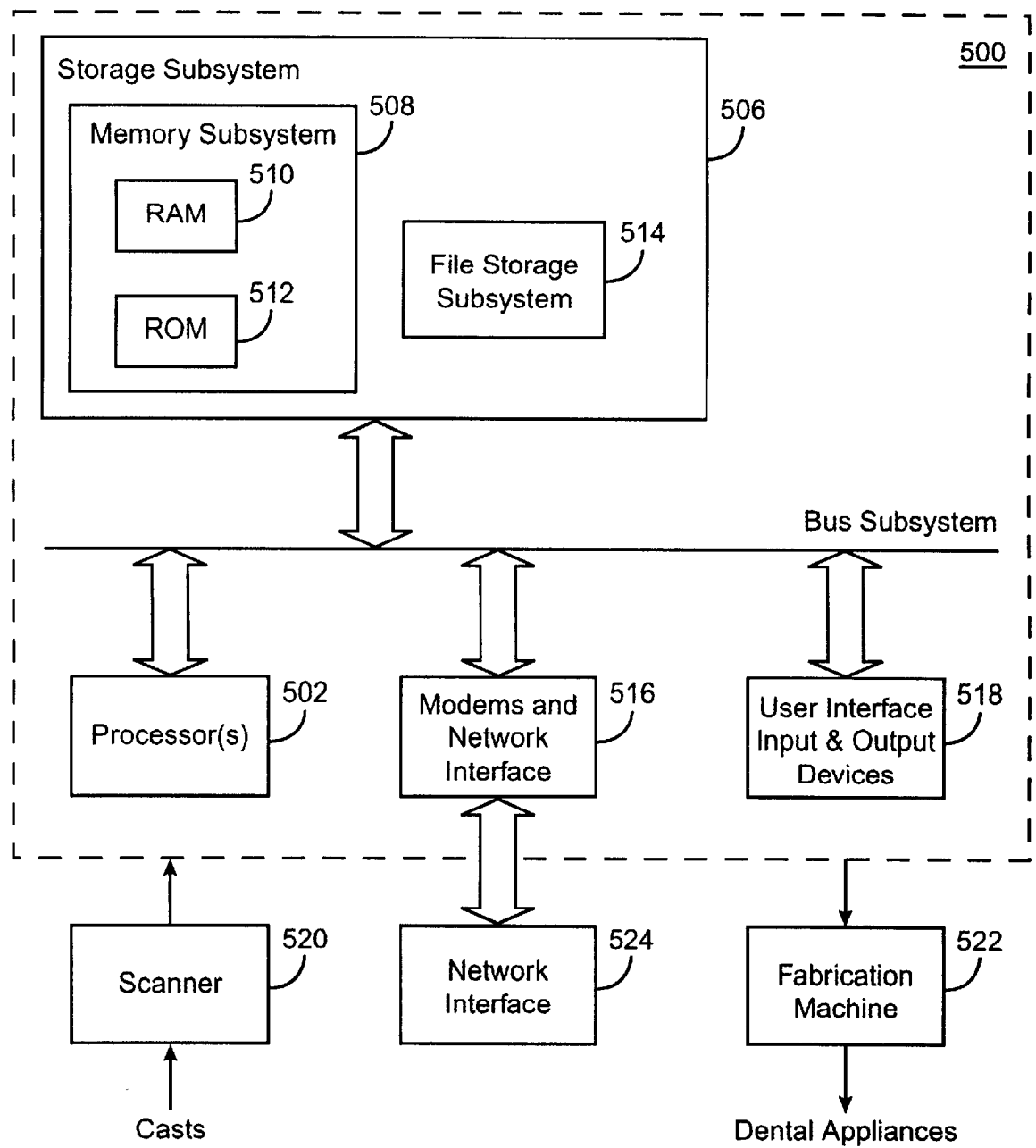
FIG. 10 is a block diagram illustrating a system for generating appliances in accordance with the present invention.

FIG. 10 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Figure 11:
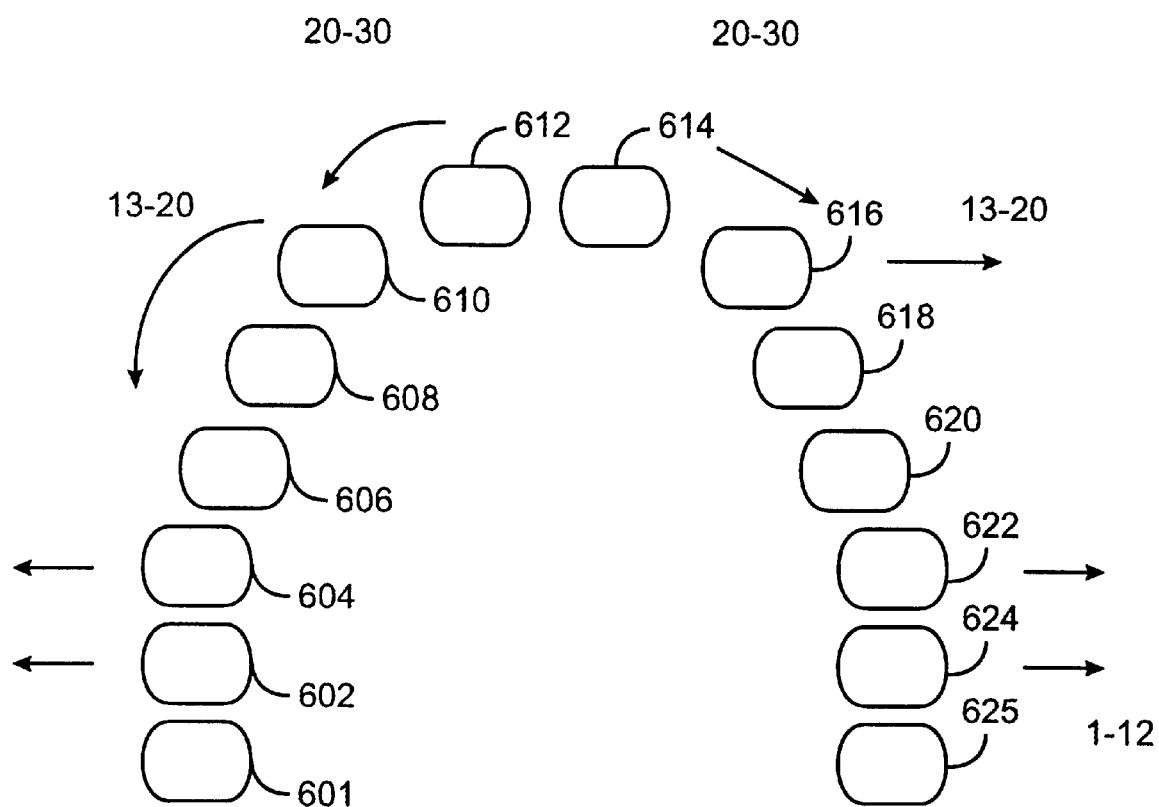
FIG. 11 is a diagram of a set of teeth that need to be moved in an expansion pattern.

The system of FIG. 10 can generate a series of appliances as defined by a treatment plan. The treatment plan can be specified by a treating professional such as a dentist or an orthodontist, among others. FIGS. 11–16 illustrate exemplary treatment specifications using a tooth movement planning system. FIG. 11 shows an exemplary set of fourteen teeth numbered 601, 602, 604, 606, 608, 610, 612, 614, 616, 618, 620, 622, 624 and 625. In the example of FIG. 11, teeth 601, 602, 604 need to move or expand toward the left side of the diagram, while teeth 606, 608, 610 and 612 need a curvilinear expansion movement toward the left also. Correspondingly, teeth 614, 616 and 618 need to moved to the right side of the diagram in a curvilinear expansion, and teeth 618, 620, 622, 624 and 625 need to be moved to the right. The end result of the prescription exemplified in FIG. 11 is that teeth are moved in an expansion pattern.

Figure 12:
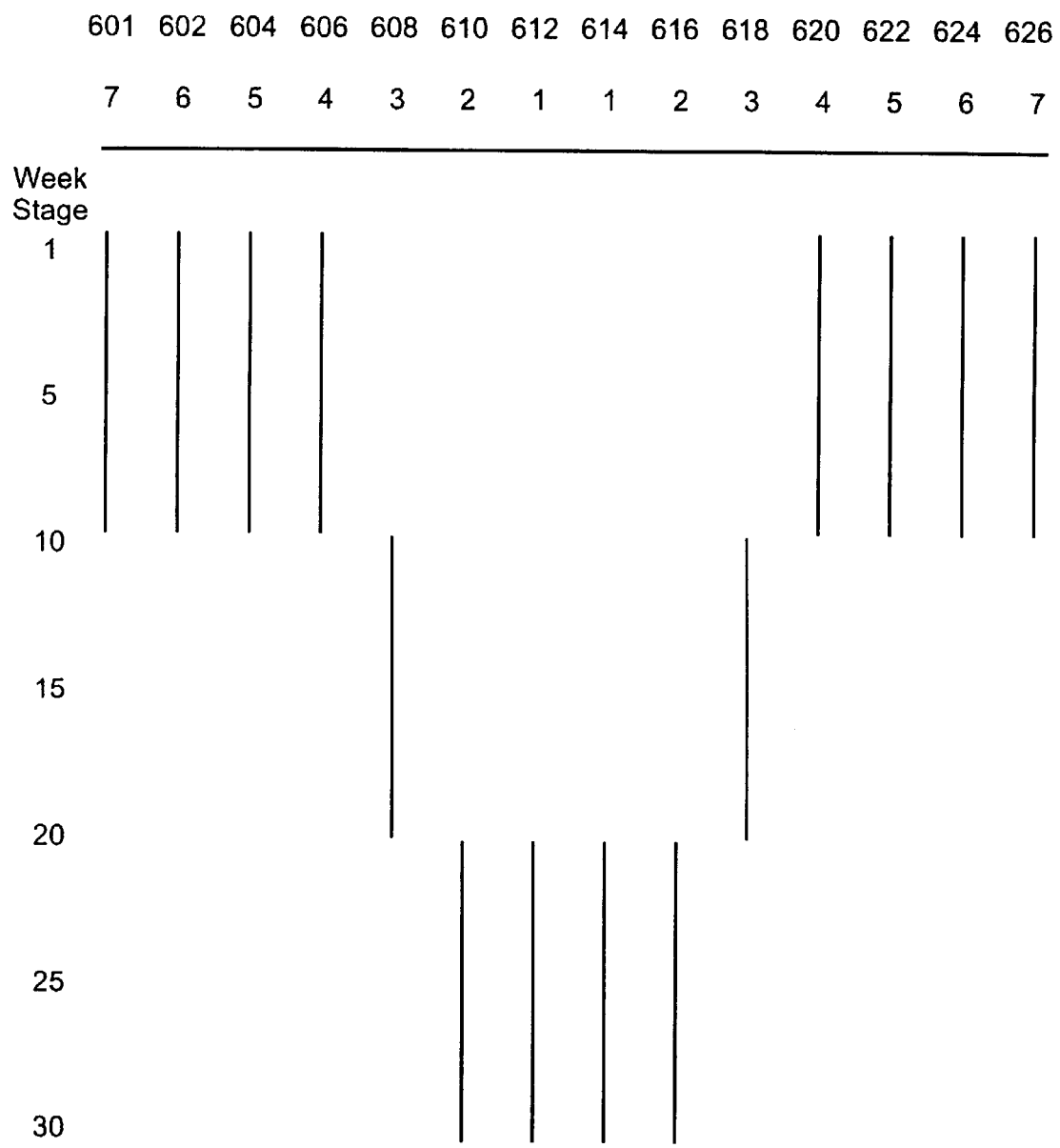
FIG. 12 is an exemplary two-dimensional diagram illustrating the movement of each tooth in the diagram of FIG. 11.

Turning now to FIG. 12, a diagrammatic illustration of the movement of FIG. 11 as specified on a two-dimensional array is shown. In FIG. 12, the top row identifies the tooth identification, while the left column number shows the stage sequence for each tooth. In this case, each stage takes approximately two weeks, although the duration can be increased or decreased. In the example of FIG. 12, the tooth 601 is moved between stages 1–10. Similarly, teeth 602, 604, 606 are moved between stages 1–10. In stages 10–20, tooth 608 is moved. Further, in stages 20–30, teeth 610–616 are moved. Tooth 618 is moved between stages 10–20. Also, teeth 620, 622, 624 and 625 are moved in stages 1–10. The net result as specified by the two-dimensional array is an expansion movement pattern.

Although FIGS. 13–16 show an exemplary expansion movement pattern, other patterns can be specified using the two-dimensional array as well. These patterns can be incorporated into a library of movements. For a given initial position of patient teeth and a final corrected position, the system generates in-between stages by finding the stage positions of each tooth in accordance with a selected movement. FIGS. 13–16 show exemplary movement patterns, namely an X-type movement, an A-type movement, a V-type movement, and an XX-type movement, among others. These exemplary movement patterns will be discussed next.

Figure 13:
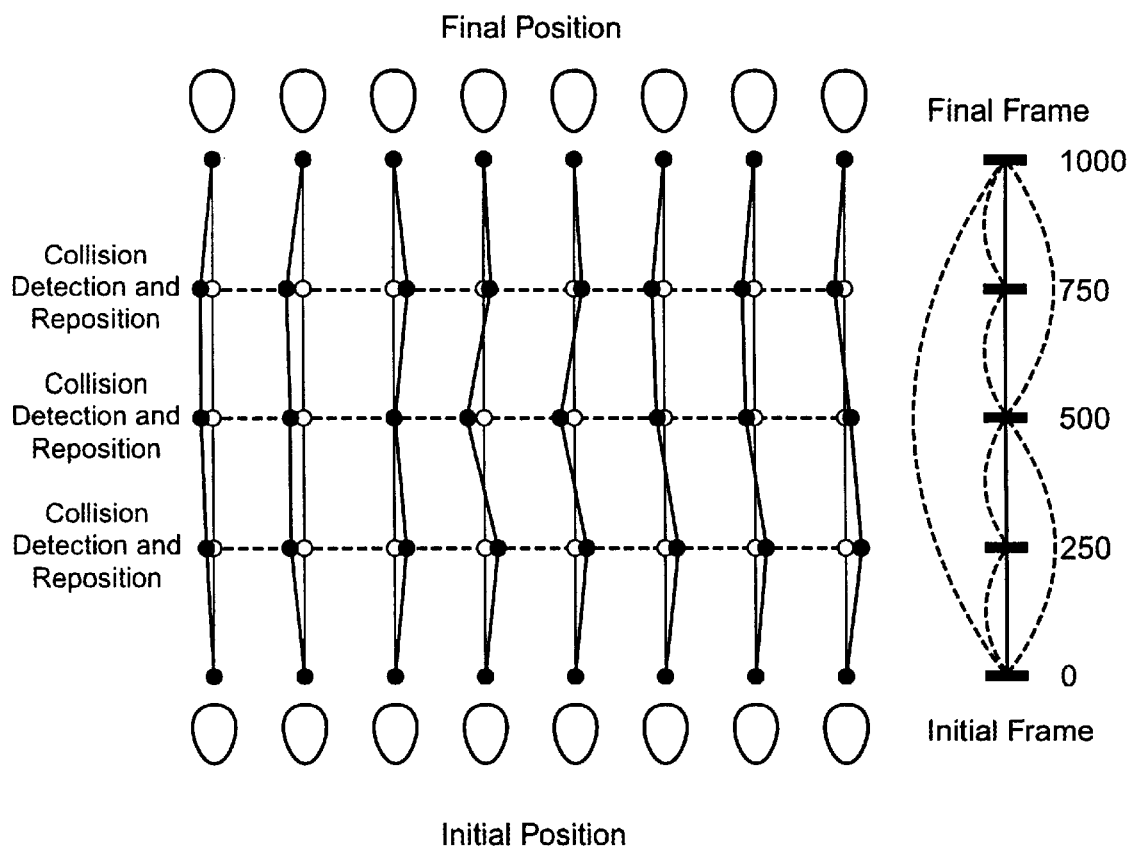
FIG. 13 shows an exemplary X-type movement.

An exemplary X-type movement is shown in FIG. 13. The X-type movement is also known as an 'All Equal Movement'. In this movement, all teeth in a given group are moving at the same time. The tooth path is determined by dividing a starting frame containing the teeth into half frames and recursively determines intermediate paths in each half. The recursion stops when the moving distance in each frame meets a given criterion. Once the movements are done, the system adjusts teeth movements so that each frame does not exceed one or more distance constraints.

Figure 14:
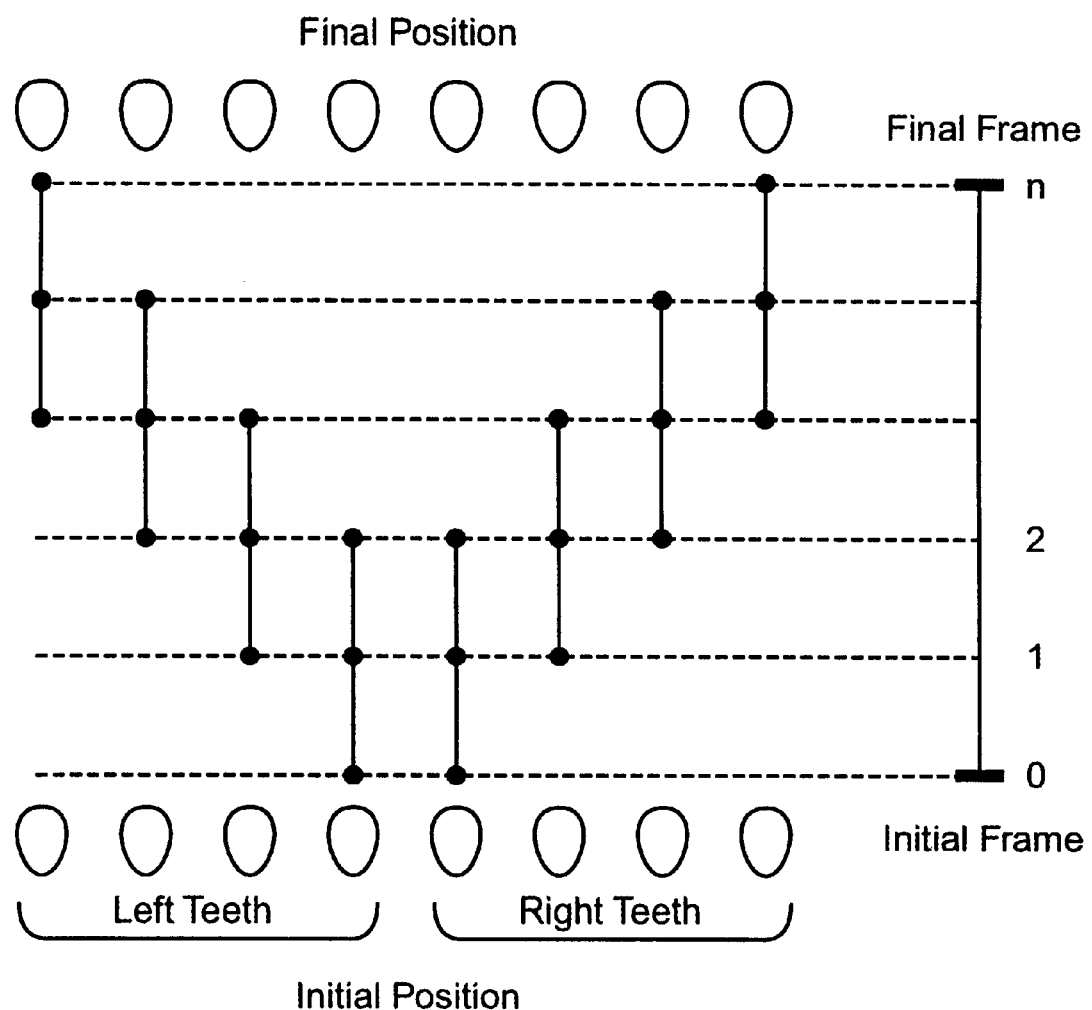
FIG. 14 shows an exemplary A-type movement.

Next, the A-type movement is discussed. In this type of movement, the anterior tooth moves first, followed by the posterior teeth. The movement looks like an A character as the front tooth is moving ahead of the next tooth. In each tooth, the next tooth starts to move when the current tooth reaches midway to the current tooth's goal position. The diagram of the A type movement is shown in FIG. 14.

Figure 15:
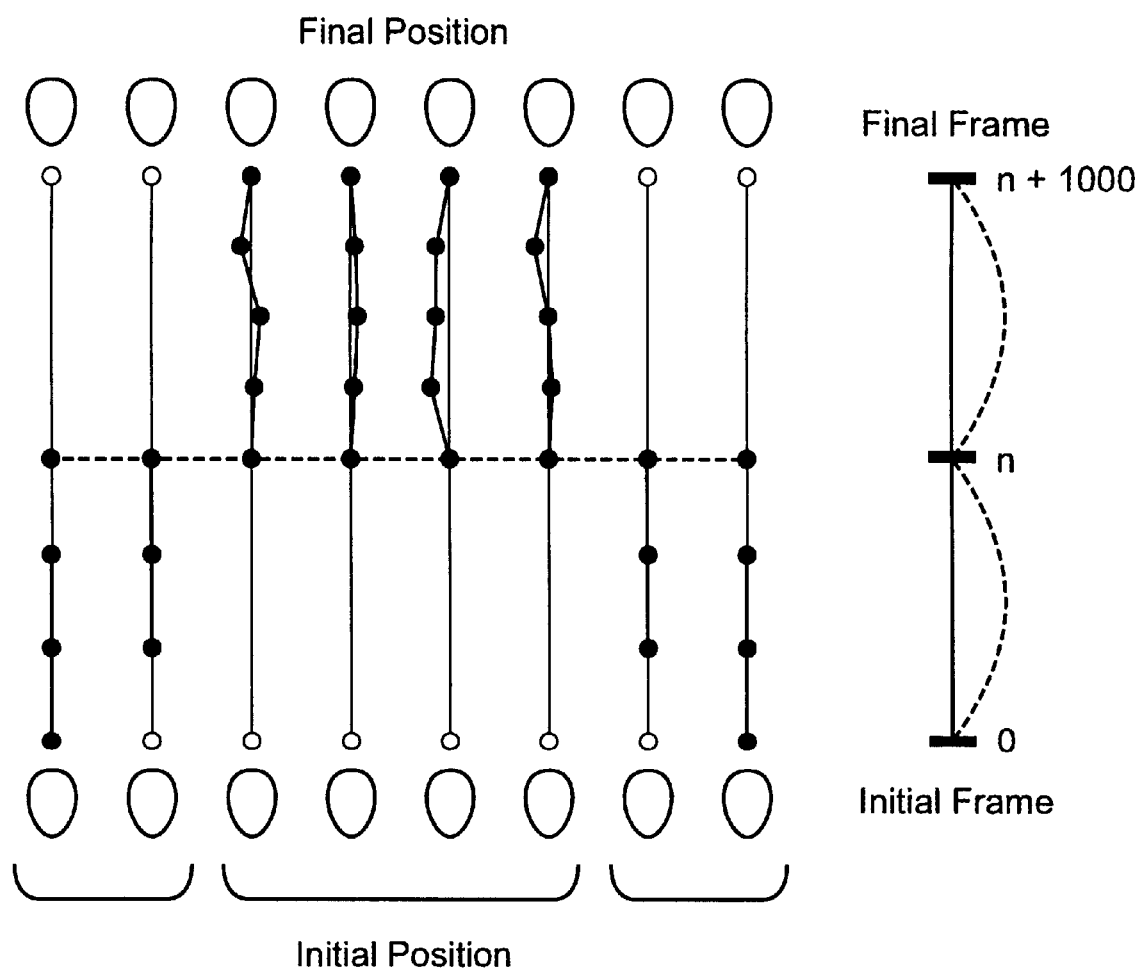
FIG. 15 shows an exemplary V-type movement.

The V-type movement is shown in FIG. 15. Conceptually, the V type movement is reverse of A type movement: the rear teeth move first then the next front teeth follow. In one implementation, a reverse A movement is done for posterior teeth, while the anterior teeth go through an X type movement.

Figure 16:
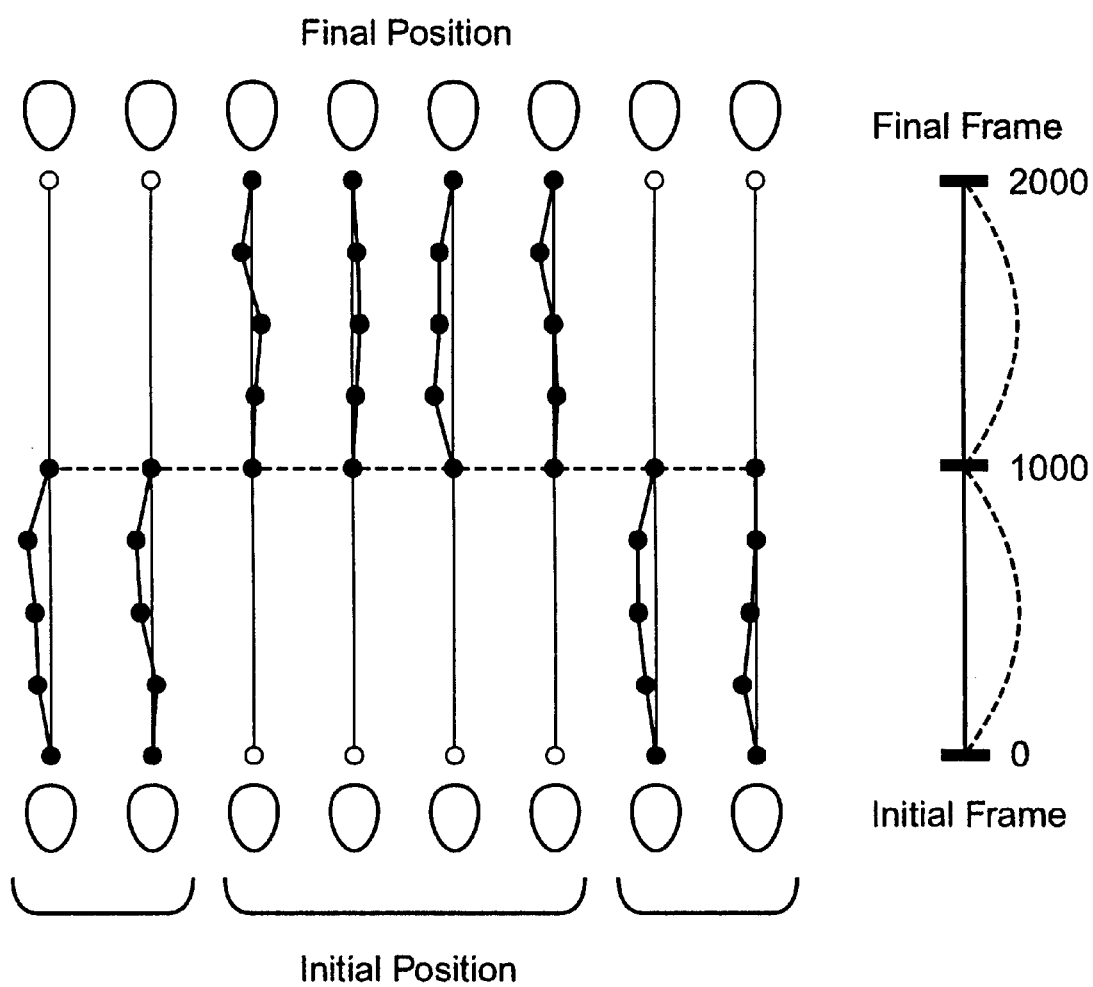
FIG. 16 shows an exemplary XX-type movement.

FIG. 16 shows an XX type movement, which involves two all equal movement. Posterior teeth go through an all equal movement (X-type) first and the anterior teeth go through the all equal movement.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

Further, while the invention has been shown and described with reference to an embodiment thereof, those skilled in the art will understand that the above and other changes in form and detail may be made without departing from the spirit and scope of the following claims.

What is claimed is:

1. A computer-implemented method to implement a treatment plan, the method comprising:
   specifying tooth movement patterns using a two-dimensional array; and
   generating treatment paths to move the teeth in accordance with a specified pattern, wherein generating treatment paths comprises generating more than one candidate treatment path for each tooth and providing a graphical display of each candidate treatment path to a human user for selection.

2. The method of claim 1, wherein the treatment paths are modified by one or more constraints.

3. The method of claim 2, wherein one of the constraints relates to teeth crowding.

4. The method of claim 2, wherein one of the constraints relates to teeth spacing.

5. The method of claim 2, wherein one of the constraints relates to teeth extraction.

6. The method of claim 2, wherein one of the constraints relates to teeth stripping.

7. The method of claim 2, wherein one of the constraints relates to teeth rotation.

8. The method of claim 7, wherein the teeth are rotated approximately five and ten degrees (per stage).

9. The method of claim 2, wherein one of the constraints relates to teeth movement.

10. The method of claim 9, wherein the teeth are incrementally moved in one or more stages (per stage).

11. The method of claim 10, wherein each tooth is moved approximately 0.2 mm to approximately 0.4 mm in each stage.

12. The method of claim 2, wherein the constraints are stored in an array.

13. The method of claim 12, wherein one dimension of the array identifies each stage in the teeth movement.

14. The method of claim 12, wherein one dimension of the array identifies each stage in the teeth movement.

15. The method of claim 12, wherein one dimension of the array identifies a unique tooth.

16. The method of claim 12, wherein one dimension of the array identifies each stage in the teeth movement and one dimension of the array identifies a unique tooth.

17. The method of claim 16, further comprising specifying tooth movement by indicating a start stage and an end stage for a tooth.

18. The method of claim 1, wherein generating the treatment paths includes determining the minimum amount of transformation required to move each tooth from the initial position to the final position and creating each treatment path to require only the minimum amount of movement.

19. The method of claim 1, wherein generating the treatment path includes generating intermediate positions for at least one tooth between which the tooth undergoes translational movements of equal sizes.

20. The method of claim 1, wherein generating the treatment path includes generating intermediate positions for at least one tooth between which the tooth undergoes translational movements of unequal sizes.

21. The method of claim 1, further comprising applying a set of rules to detect any collisions that will occur as the patient's teeth move along the treatment paths.

22. The method of claim 1, further comprising receiving information indicating whether the patient's teeth are following the treatment paths and, if not, using the information to revise the treatment paths.

23. The method of claim 1, further comprising rendering a three-dimensional (3D) graphical representation of the teeth at the positions corresponding to a selected data set.

24. The method of claim 23, further comprising animating the graphical representation of the teeth to provide a visual display of the movement of the teeth along the treatment paths.

25. The method of claim 24, further comprising providing a graphical interface, with components representing the control buttons on a video cassette recorder, which a human user can manipulate to control the animation.

26. The method of claim 1, further comprising determining one or more tooth paths based on the selected tooth movement pattern.

27. The method of claim 26, wherein determining a tooth path comprises finding a collision free shortest path between an initial position and a final position for one or more teeth.

28. The method of claim 1, further comprising selecting one or more clinical treatment prescriptions.

29. The method of claim 28, wherein the clinical treatment prescription includes at least one of the following: space closure, reproximation, dental expansion, flaring, distalization, and lower incisor extraction.

30. The method of claim 1, further comprising dividing a path for one or more teeth into the series of stages.

31. The method of claim 1, further comprising generating an appliance for each treatment stage.

32. The method of claim 31, wherein the appliance is either a removable appliance or a fixed appliance.

33. The method of claim 1, further comprising generating a three-dimensional model for the teeth for each treatment stage.

34. A computer-implemented method to implement a treatment plan, the method comprising:
   specifying tooth movement patterns using a two-dimensional array;
   generating treatment paths to move the teeth in accordance with a specified pattern; and
   rendering a three-dimensional (3D) animated graphical representation of the teeth at positions corresponding to a selected data set to provide a visual display of the movement of the teeth along the treatment paths.

35. The method of claim 34, wherein the treatment paths are modified by one or more constraints.

36. The method of claim 35, wherein one of the constraints relates to teeth crowding.

37. The method of claim 35, wherein one of the constraints relates to teeth spacing.

38. The method of claim 35, wherein one of the constraints relates to teeth extraction.

39. The method of claim 35, wherein one of the constraints relates to teeth stripping.

40. The method of claim 35, wherein one of the constraints relates to teeth rotation.

41. The method of claim 40, wherein the teeth are rotated approximately five and ten degrees (per stage).

42. The method of claim 35, wherein one of the constraints relates to teeth movement.

43. The method of claim 42, wherein the teeth are incrementally moved in one or more stages (per stage).

44. The method of claim 43, wherein each tooth is moved approximately 0.2 mm to approximately 0.4 mm in each stage.

45. The method of claim 35, wherein the constraints are stored in an array.

46. The method of claim 45, wherein one dimension of the stage in the teeth movement.

47. The method of claim 45, wherein one dimension of the array identifies each stage in the teeth movement.

48. The method of claim 45, wherein one dimension of the array identifies a unique tooth.

49. The method of claim 45, wherein one dimension of the array identifies each stage in the teeth movement and one dimension of the array identifies a unique tooth.

50. The method of claim 49, further comprising specifying tooth movement by indicating a start stage and an end stage for a tooth.

51. The method of claim 35, further comprising generating a three-dimensional model for the teeth for each treatment stage.

52. The method of claim 34, wherein generating the treatment paths includes determining the minimum amount of transformation required to move each tooth from the initial position to the final position and creating each treatment path to require only the minimum amount of movement.

53. The method of claim 34, wherein generating the treatment path includes generating intermediate positions for at least one tooth between which the tooth undergoes translational movements of equal sizes.

54. The method of claim 34, wherein generating the treatment path includes generating intermediate positions for at least one tooth between which the tooth undergoes translational movements of unequal sizes.

55. The method of claim 34, further comprising applying a set of rules to detect any collisions that will occur as the patient's teeth move along the treatment paths.

56. The method of claim 34, further comprising receiving information indicating whether the patient's teeth are following the treatment paths and, if not, using the information to revise the treatment paths.

57. The method of claim 34, wherein generating treatment paths comprises generating more than one candidate treatment path for each tooth and providing a graphical display of each candidate treatment path to a human user for selection.

58. The method of claim 34, comprising providing a graphical interface, with components representing the control buttons on a video cassette recorder, which a human user can manipulate to control the animation.

59. The method of claim 34, further comprising determining one or more tooth paths based on the selected tooth movement pattern.

60. The method of claim 59, wherein determining a tooth path comprises finding a collision free shortest path between an initial position and a final position for one or more teeth.

61. The method of claim 34, further comprising selecting one or more clinical treatment prescriptions.

62. The method of claim 61, wherein the clinical treatment prescription includes at least one of the following: space closure, reproximation, dental expansion, flaring, distalization, and lower incisor extraction.

63. The method of claim 34, further comprising dividing a path for one or more teeth into the series of stages.

64. The method of claim 34, further comprising generating an appliance for each treatment stage.

65. The method of claim 64, wherein the appliance is either a removable appliance or a fixed appliance.

* * * * *